US006855331B2

(12) United States Patent
Vook et al.

(10) Patent No.: US 6,855,331 B2
(45) Date of Patent: Feb. 15, 2005

(54) SUSTAINED RELEASE HYDROPHOBIC BIOACTIVE PLGA MICROSPHERES

(75) Inventors: Noelle Christine Vook, Schaumburg, IL (US); Elliott Jacob, Silver Spring, MD (US); Jean A. Setterstrom, Alpharetta, GA (US); John van Hamont, West Point, NY (US); William Vaughan, Silver Spring, MD (US); Ha Duong, Montclair, CA (US)

(73) Assignee: The United States of America as represented by the Secretary of the Army, Washington, DC (US)

(*) Notice: Subject to any disclaimer, the term of this patent is extended or adjusted under 35 U.S.C. 154(b) by 75 days.

(21) Appl. No.: 10/165,975

(22) Filed: Jun. 10, 2002

(65) Prior Publication Data

US 2003/0129233 A1 Jul. 10, 2003

Related U.S. Application Data

(63) Continuation of application No. 08/920,326, filed on Aug. 21, 1997, now Pat. No. 6,447,796, and a continuation-in-part of application No. 08/789,734, filed on Jan. 27, 1997, now Pat. No. 6,309,669, which is a continuation-in-part of application No. 08/698,896, filed on Aug. 16, 1996, now Pat. No. 5,705,197, and a continuation-in-part of application No. 08/675,895, filed on Jul. 5, 1996, now Pat. No. 6,217,911, which is a continuation-in-part of application No. 08/590,973, filed on Jan. 24, 1996, now abandoned, which is a continuation-in-part of application No. 08/446,149, filed on May 22, 1995, now abandoned, and a continuation-in-part of application No. 08/446,148, filed on May 22, 1995, now Pat. No. 6,410,056, which is a continuation-in-part of application No. 08/242,960, filed on May 16, 1994, now Pat. No. 5,693,343.

(51) Int. Cl.⁷ .......................... A61F 13/00; A61F 2/00; A61K 9/52; A61K 9/50
(52) U.S. Cl. ..................... 424/422; 424/426; 424/457; 424/468; 424/501
(58) Field of Search ............................... 424/501, 422, 424/426, 457, 468

(56) References Cited

U.S. PATENT DOCUMENTS

| | | | |
|---|---|---|---|
| 3,540,444 A | 11/1970 | Moreland | 128/173 |
| 3,773,919 A | 11/1973 | Boswell | 424/19 |
| 3,788,315 A | 1/1974 | Laurens | 128/173 H |
| 4,166,800 A | 9/1979 | Fong | 252/316 |
| 4,384,975 A | 5/1983 | Fong | 427/213.36 |
| 4,530,840 A | 7/1985 | Tice et al. | 514/179 |
| 4,542,025 A | 9/1985 | Tice et al. | 424/78 |
| 4,585,482 A | 4/1986 | Tice et al. | 106/15.05 |
| 4,622,244 A | 11/1986 | Lapka et al. | 427/213.32 |
| 4,637,905 A | 1/1987 | Gardner | 264/4.3 |
| 4,675,189 A | 6/1987 | Kent et al. | 424/490 |
| 4,798,786 A | 1/1989 | Tice et al. | 435/177 |
| 4,835,139 A | 5/1989 | Tice et al. | 514/15 |
| 4,863,735 A | 9/1989 | Kohn et al. | 524/422 |
| 4,897,268 A | 1/1990 | Tice et al. | 424/422 |
| 4,938,763 A | 7/1990 | Dunn et al. | 604/891.1 |
| 4,941,880 A | 7/1990 | Burns | 604/143 |
| 5,000,886 A | 3/1991 | Lawter et al. | 264/4.3 |
| 5,019,096 A | 5/1991 | Fox, Jr. et al. | 623/1 |
| 5,059,187 A | 10/1991 | Sperry et al. | 604/290 |
| 5,064,413 A | 11/1991 | McKinnon et al. | 604/70 |
| 5,075,109 A | 12/1991 | Tice et al. | 424/88 |
| 5,102,872 A | 4/1992 | Singh et al. | 514/21 |
| 5,129,825 A | 7/1992 | Discko, Jr. | 433/90 |
| 5,133,701 A | 7/1992 | Han | 604/289 |
| 5,236,355 A | 8/1993 | Brizzolara et al. | 433/80 |
| 5,278,202 A | 1/1994 | Dunn et al. | 523/113 |
| 5,290,494 A | 3/1994 | Coombes et al. | 264/41 |
| 5,360,610 A | 11/1994 | Tice et al. | 424/426 |
| 5,384,133 A | 1/1995 | Boyes et al. | 424/501 |
| 5,407,609 A | 4/1995 | Tice et al. | 264/46 |
| 5,417,986 A | 5/1995 | Reid et al. | 424/499 |
| 5,429,822 A | 7/1995 | Gresser et al. | 424/426 |
| 5,648,096 A | 7/1997 | Gander et al. | 424/489 |
| 5,650,173 A | 7/1997 | Ramstack et al. | 424/489 |
| 5,705,197 A * | 1/1998 | Van Hamont et al. | 424/501 |
| 6,447,796 B1 * | 9/2002 | Vook et al. | 424/422 |

FOREIGN PATENT DOCUMENTS

EP 0052510 B2 10/1994 ................. 435/177

OTHER PUBLICATIONS

Gilding, Biodegradable polymers for use in surgery–polyglycolic/poly (ac c acid) homo– and copolymers: 1, Polymer, vol. 20, Dec. 1979, pp1459–1464.
Biotechnology News, Aug. 22, 1997, vol. 17, No. 20, Topical DNA vaccine elicits immune response.
Hall, et al., Purification and Analysis of Colonization Factor Antigen 1, Coli Surface Antigen 1, and Coli Surface ANtigen 3 Fimbriac from Enterotoxigenic *Escherichia coli*, Journal of Bacteriology, Nov. 1989, p6372–6374, vol. 171, No. 11.
Evans, et al. Purification and Characterization of the CFR/I Antigen of Enterotoxigenic *Escherichia coli*, Infection and Immunity, Aug. 1979, p 738–748, vol. 25.
Karjalainen, et al., Molecular Cloning and Nucleotide Sequence of the Colonization Factor Antigen I Gene of *Escherichia coil*, Infection and Immunity, Apr. 1989, p1126–1130, vol. 57.
Jeyanthl, et al., Novel, Burst Free Programmable Biodegradable Microspheres For Controlled Release of Polypeptides, Proceedings Int. Symp. control Release Bioact. Mater. (1996) p351–352/.
Yeh, A novel emulsification–solvent extraction technique for production of protein loaded biodegradable microparticles for vaccine and drug delivery, Journal of Controlled Release, 33 (1995) 437–445.

(List continued on next page.)

Primary Examiner—Theodore J. Criares
(74) Attorney, Agent, or Firm—Elizabeth Arwine

(57) ABSTRACT

A controlled release microcapsulate pharmaceutical formulation for burst-free, sustained, programmable release of hydrophobic bioactive agent over a duration from 24 hours to 100 days comprising: and a blend of end-capped uncapped biocompatible, biodegradable poly(lactide/glycolide).

13 Claims, 21 Drawing Sheets

OTHER PUBLICATIONS

Yan, Characterization and morphological analysis of protein–loaded poly(lactide–co–glycolide) microparticles prepared by watewr–in–oil–in–water emulsion technique, Journal of Controlled Release, 32 (1994) 231–241.

Wang, et al., Influence of formulation methods on the in vitro controlled release of protein from poly (ester) microspheres Journal of Controlled Release, 17 (1991) 23–32.

Brown, Wonder Drugs' Losing Healing Aura, The Washing Post, Jun. 26, 1995, A section.

Setterstrom, Controlled Release of Antibiotics From biodegradable Microcapsules For Wound infection Control, Chemical Abstracts, 1983, pp215–226.

Perez–Casal, et al., Gene Encoding the Major Subunit of CS1 Pili of Human Enterotoxigenic *Escherichia coli*, Infection and Immunity, Nov., 1990, p 3594–3600, vol. 58, No. 11.

Jordi, et al., Analysis of the first two genes of the CS1 fimbrial operon in human entertoxigenic *Escherichia coli* of serotype 0139: H28, FEMS Microbiology Letters 80, (1991) p265–270.

Tan, et al., Mapping the Antigenic Epitopes of Human Dihydrofolate Reductase by Systematic Synthesis of Peptides on solid Supports, The Journal of Biological Chemistry, vol. 265, No. 14, Issue of May 15, pp. 8022–8026 (1990).

McConnel, et al., Antigenic homology within human enterotoxigenic *Esherichia coli* fimbrial colonization factor antigens: CFA/I, coil–surface–associated antigens (CS)1, CS2, CS4 and CS17, FEMS Microbiology Letters 61 (1989) 105–108.

Van der Zee, Efficient mapping and characterization of a T cell epitope by the simultaneous synthesis of multiple peptides, Eur. J. Immunol. 1989, 19: 43–47.

Cassels, et al., Analysis of *Escherichia coli* Colonization Factor Antigen I Linear B–Cell Epitopes, as Determined by Primate Responses, following Protein Sequence Verification, Infection and Immunity, Jun. 1992, p. 2174–2181, vol. 60, No. 6.

Romagnoli, et al. Peptide–MHC Interaction: A Rational Approach to Vaccine Design, Inter, RE. Immunol. 6, 1990, 00 61–73.

Maister, First Oral AIDS Vaccine Trials Near, BioWorld Today, Tuesday, Apr. 19, 1994, p. 4.

Rognan, et al., Molecular Modeling of an Antigenic Complex Between a Viral Peptide and a Class I Major Histocompatibility Glycoprotein, Proteins Structure, Function and Genetics 13 70–85 (1992).

Brown, A hypothetical model of the foreign antigen blinding site of Class II histocompatibility molecules, Nature, vol. 332, Apr. 28, 1988, p845–850.

* cited by examiner

FORMULATION: TX 57

CORE LOAD: 10.16%

TOTAL # 2300-46　　　　　　　　　　　　　　FILE: TX57.1

SIZE (um) — SENSOR: LE400-1　CAL: 96119065E.-IMS　THRESHOLD: 0.000%

FORMULATION: TX 20%

CORE LOAD: 18.38%

TOTAL # 84768

FILE: TX20%111.0

SIZE(um)→SENSOR: LE400-1 CAL: 9611906E.IMS THRESHOLD: 0.000%

FORMULATION: TX 40%

CORE LOAD: 37.77%

TOTAL #132846    FILE: TX40%.0

FORMULATION: TX 50%

CORE LOAD: 47.74%

TOTAL # 116422　　　　　　　　　　　　　　　　FILE: TX50%.0

POPULATION DISTRIBUTION

SIZE:(um)→SENSOR:LE400-1 CAL:9611506E.IMS THRESHOLD:0.000%

FORMULATION: TX MEDISORB

CORE LOAD: 8.60%
POLYMER COMPONENTS: 100% MEDISORB POLYMER-LOW i.v.

TOTAL #62866          FILE:TXMD.O

SIZE(um)→SENSOR:LE400-1 CAL:8611906E.IMS THRESHOLD:0.000%

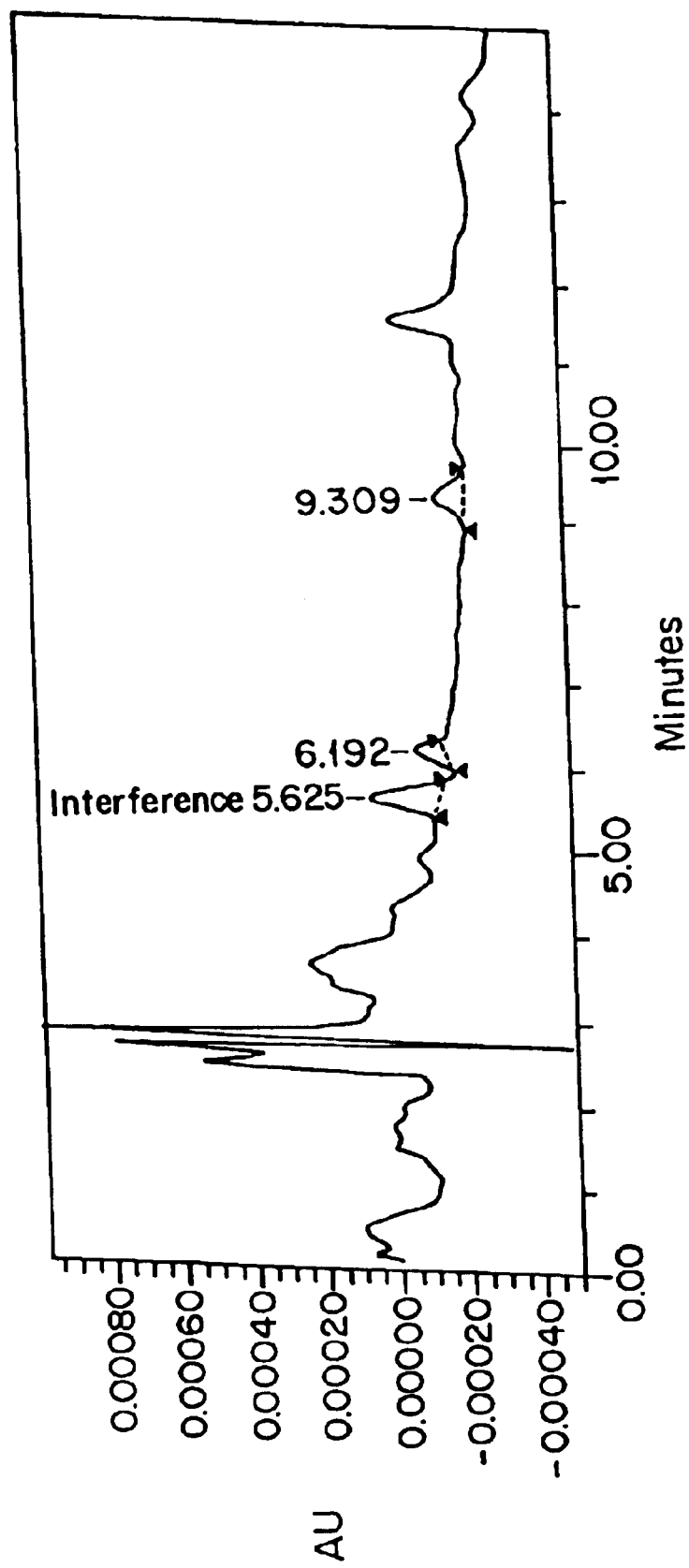

SUSTAINED RELEASE HYDROPHOBIC BIOACTIVE PLGA MICROSPHERES

CROSS-REFERENCE

This application is a continuation application of U.S. patent application Ser. No. 08/920,326, filed Aug. 21, 1997 now U.S. Pat. No. 6,447,796 which a continuation-in-part of U.S. patent application Ser. No. 08/698,896 filed Aug. 16, 1996 now U.S. Pat. No. 5,705,197, which in turn is a continuation-in-part of U.S. patent application Ser. No. 08/242,960 filed May 16, 1994 now U.S. Pat. No. 5,693,343; U.S. patent application Ser. No. 08/675,895 filed Jul. 5, 1996 now U.S. Pat. No. 6,217,911; and U.S. patent application Ser. No. 08/789,734 filed Jan. 27, 1997 now U.S. Pat. No. 6,309,669 which in turn is a continuation-in-part of U.S. patent application Ser. No. 08/590,973 filed Jan. 24, 1996 now abandoned which in turn is a continuation-in-part of U.S. patent application Ser. No. 08/446,148 filed May 22, 1995 now abandoned and U.S. patent application Ser. No. 08/446,148 filed May 22, 1995 now U.S. Pat. No. 6,410,056, and incorporates in its entirety, the contents of U.S. patent application Ser. Nos. 08/698,896; 08/242,960; 08/675,895; 08/789/734; 08/590,973; 08/446,149 and 08/446,148.

GOVERNMENT INTEREST

The invention described herein may be manufactured, licensed and used by or for governmental purposes without the payment of any royalties to us thereon.

FIELD OF THE INVENTION

This invention relates to providing novel pharmaceutical compositions for local delivery and burst-free programmable, sustained release of hydrophobic drugs from biocompatible, biodegradable poly (DL-lactide-co-glycolide) (PLGA) microspheres. The resulting product is administered locally into soft tissues by sub-cutaneous or intra-muscular injection where it will locally sustain release the drug.

This invention relates generally to providing novel blend of end-capped and uncapped providing novel biocompatible and biodegradable PLGA microspheres for burst-free programmable sustained release of hydrophobic biologically active agents which degrade over a period of up to 100 days in an aqueous physiological environment. The active agents contemplated within the scope of this invention includes the delivery of poly-peptide antibiotics, antimalarials, antituberculosis drugs, anesthetics, analgesics, anticancer agents, antiparasitic agents, antibacterial agents, antifungal agents, antiinflammatory agents, immunosuppressive agents, immunostimulatory agents, dentinal desensitizers, odor masking agents, nutritional agents, antioxidants, and insulins.

The invention also relates especially to providing novel pharmaceutical compositions for sustained release of compounds for treating cancer, inflammatory and/or autoimmune disorders from PLGA microspheres.

BACKGROUND OF THE INVENTION

This invention is particularly effective for the localized delivery of chemotherapeutic hydrophobic anticancer agents, inclusive of paclitaxel(taxol)doxorubicin, 5-fluorouracil, campthothecin, cisplatin, and metronidazole, their corresponding derivatives and functionally equivalents, and combinations thereof from PLGA microspheres.

One-third of all individuals in the United States of America (U.S.) alone will develop cancer.

Although the five-year survival rate has risen dramatically to nearly fifty percent as a resulting progress in early diagnosis and the therapy, cancer still remains second only to cardiac disease as a cause of death in the U.S. twenty percent of Americans die from cancer, half due to lung, breast, and colon-rectal cancer.

Breast cancer is the second leading cause of death in women in the U.S. Approximately 135,000 women are diagnosed with and 42,000 women die from breast cancer annually (1). Breast cancer treatment plans include a combination of surgery, radiotherapy, and chemotherapy (CT). The general treatment plan for stage I and II breast cancer is conservative surgery and radiotherapy (2,3,4,5). The general treatment plan for stage III and IV breast cancer is a combination of surgery, radiotherapy, and systemic CT using chemotherapeutic agents such as taxol (6,7,8,9,10).

Taxol treatment is recommended for the treatment of breast cancer when CT for metastatic disease has failed or when disease relapse has occurred within 6 months of adjuvant CT. Advantages of taxol treatment include: (1) lack of cardiotoxicity; (2) a mechanism of action, the stabilization of microtubules, which targets a large percentage of tumor cells, as opposed to normal cells; and (3) inhibition of angiogensis (11,12). Taxol is systemically administered intravenously (i.v.), primarily as a bolus administration. Systemic CT using taxol, as well as other chemotherapeutic drugs, is highly effective, in terms of additional years of life gained as a result of therapy; however, there are many problems associated with this treatment regimen.

CT drugs are high by cytotoxic (13), and typically, large doses of CT drugs are needed to produce an optimal therapeutic response(13, 14); therefore, CT drugs have a low therapeutic index(13). Side effects commonly seen with taxol CT include: nausea, vomiting, fever, weight changes, musculoskeletal pain, neuropathy, general malaise, immune dysfunction, and the development of tumor resistance to taxol (9,15,16).

An additional side effect seen in patients treated with taxol is a severe hypersensitivity reaction due to Cremophor EL, taxol's solubilizing agent (17). This side effect is controlled via patient pre-medication using a combination of corticosteroids, antihistamines, and histamine receptor antagonists. Often, patients become so ill during therapy that they are removed from treatment regimens or that drug dosages are lowered. The consequence of these regimen changes is fluctuating drug levels, which equates to decreased efficacy.

The problems associated with systemic taxol treatment signal the need for the development of a drug delivery system which offers a safer and a more effective means of administering toxic agents, such as taxol, to breast cancer patients, as well as to other cancer patients.

Delivery systems based on prolonged exposure to taxol have been investigated as a means to overcome the problems associated with bolus administration of taxol. These systems include infusional administration of taxol over 1,3,24, or 96 hours and administration of taxol via polymeric carrier vehicle. Infusional data suggests that cytotoxicity may be enhanced due to the increased exposure of cycling cells and has shown, in vitro, 4.4 fold less resistance in multi-drug resistant MCP-7 human breast carcinoma cells exposed to taxol for 24 hours as compared to 3 hours (16). A 96-hour taxol infusion study in patients with metastatic breast cancer showed that this infusion schedule: (1) was better tolerated than bolus administration of taxol, as evidenced by mild side effects, such as nausea and myalgia; (2) did not cause significant hypersensitivity reactions despite the omission of corticosteroid pre-treatment; (3) did not result in any cardiac, renal, or hepatic toxicity, and (4) resulted in major objective responses in 7/26 patients (26.9%), with a 6 month median response duration (16). In this trial, the predominant toxic side effect was granulocytopenia which resulted in taxol dose reduction in 3/26 patients (11.54%) and in hospitalization of 4/26 patients (15.38%).

Taxol infusion regiments offer significant advantages over bolus administration of taxol in terms of systemic toxicity, efficacy, and resistance; however, immune dysfunction still appears to be the major limiting factor in the success of this treatment regimen.

Certain chemotherapeutics such as paclitaxel (taxol) and camptothecin, which are efficacious when administered systemically must be delivered at very high dosages in order to avoid toxicity due to poor bioavailability. For example, paclitaxel (taxol) has been used systemically with efficacy in treating several human tumors, including ovarian, breast, and non-small cell lung cancer. However, maintenance of sufficient systemic levels of the drug for treatment of tumors has been associated with severe, in some cases "life-threatening" toxicity, as reported by Sarosy and Reed, J. Nat. Med. Assoc. 85(6):427–431 (1993). Paclitaxel is a high molecular weight (854), highly lipophilic deterpenoid isolated from the western yew, Taxus brevifolia, which is insoluble in water. It is normally administered intravenously by dilution into saline of the drug dissolved or suspended in polyoxyethylated castor oil. This carrier has been reported to induce an anaphylactic reaction in a number of patients (Sarosy and Reed (1993) so alternative carriers have been proposed, such as a mixed micellar formulation for parenteral administration, described by Alkan-Onyuksel, et al., Pharm. Res. 11(2), 206–212 (1994). There is also extensive non-renal clearance, with indications that the drug is removed and stored peripherally. Pharmacokinetic evidence from clinical trials (Rowinsky, E. K., et al., Cancer Res. 49:4640–4647 (1989) and animal studies (Klecker, R. W., Proc. Am. Cancer Res. 6.43:381 (1993) indicates that paclitaxel penetrates the intact blood-brain barrier poorly, if at all, and that there is no increased survival from systemic intraperitoneal injections of paclitaxel into rats with intracranial gliomas. Paclitaxol has been administered in a polymeric matrix for inhibition of scar formation in the eye, as reported by Jampel, et al., Opthalmic Surg. 22, 676–680 (1991), but has not been administered locally to inhibit tumor growth.

SUMMARY OF THE INVENTION

This invention provides a method and novel pharmaceutical compositions for local delivery and burst-free programmable sustained release of hydrophobic drugs from biocompatible, biodegradble poly (DL-lactide-co-glycolide) (PLGA) microspheres. The hydrophobic drugs are released over a time period while at the same time preserving its bioactivity and bioavailability.

It is therefore an object of the present invention to provide a chemotherapeutic composition and method of use thereof which provides for effective long term release of chemotherapeutic agents that are not stable or soluble in aqueous solutions or which have limited bioavailability in vivo for treatment of solid tumors.

It is a further object of the present invention to provide a composition and method of use for the treatment of solid tumors with chemotherapeutic agents that avoids high systemic levels of the agent and associated toxicities.

DETAILED DESCRIPTION OF THE INVENTION

Figure 1:
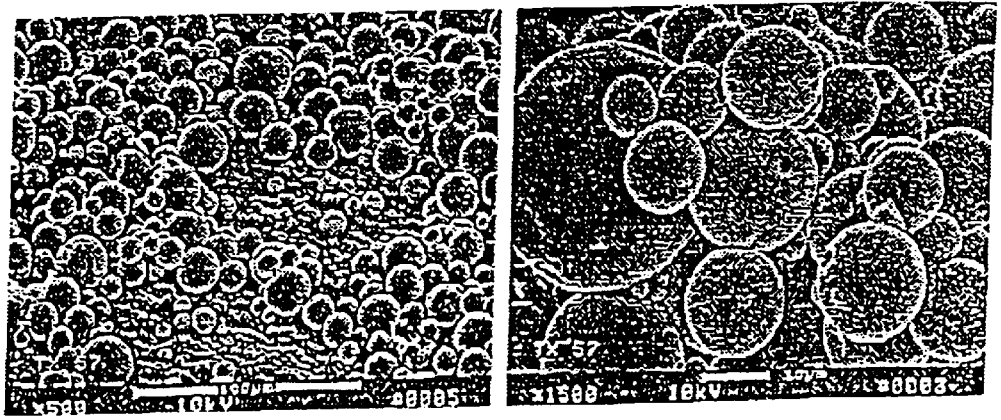
FIG. 1 shows the microsphere morphology of taxol PLGA: 10% core load formulation; Background Count Specifics: 426 particles; mean=5.05 um; median=2.74 um Taxol/PLGA Microspheres Counted: 230,046; Mean=7.75 um; Median=6.15 um.
Figure 1:
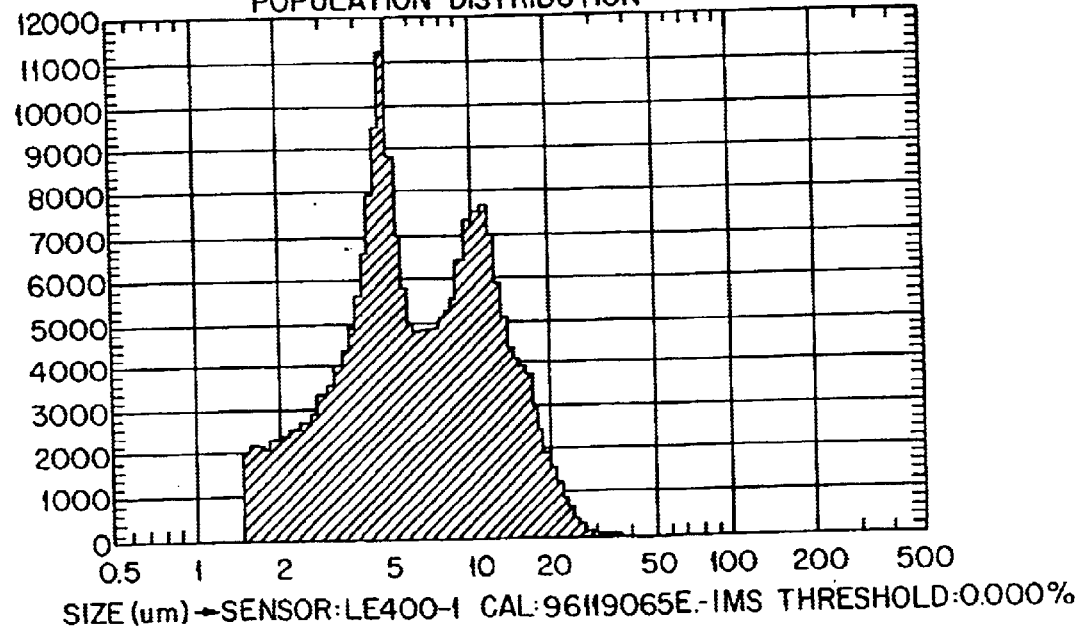

The novel compositions described herein are formulated of chemotherapeutic agent, such as paclitaxel (taxol), doxorubicin, 5-fluorouracil, campthothecin, cisplatin, metronidazole campthothecin and combinations, derivatives, or functional equivalents thereof, which are not water soluble and has poor bioavailability in vivo encapsulated into a biocompatible/biodegradable polymeric matrix or in combination with hydrophillic agents for use especially in the treatment of breast cancer.

The polymer bound taxol formulations of this invention represent another strategy to achieve prolonged exposure to taxol which appears to be more advantageous than infusion regiments. Of greatest utility are the biodegradable polymers, which include the poly(lactide-co-glycolide) (PLGA) copolymer. A variety of biodegradable polymer bound taxol formulations have been developed and have been shown to inhibit tumor growth and angiogenesis in animal models with minimal systemic toxicity; however, the release kinetics of taxol in these systems, which range from 10–25% of the drug released in approximately 50 days, are, most likely, not optimal for clinical use (18,17,11,12,19,20, 21,22). The advantages of biodegradable polymers as a carrier for taxol include: (1) complete biodegradation, requiring no follow-up surgery to remove the drug carrier when the drug supply is exhausted (23,24); (2) tissue biocompatibility (25); 3) ease of administration via s.c. ir u,n, ubhectuib (23,26,27); (4) controlled, sustained release of the encapsulated drug upon hydrolysis of the polymer(27,23, 28,24);(5) minimization or elimination of systemic toxicity, such as neutropenia 23,24,26,27); and (6) the convenience of the biodegradable polymer system itself, in terms of versatility (23,29,24,26).

Figure 4:
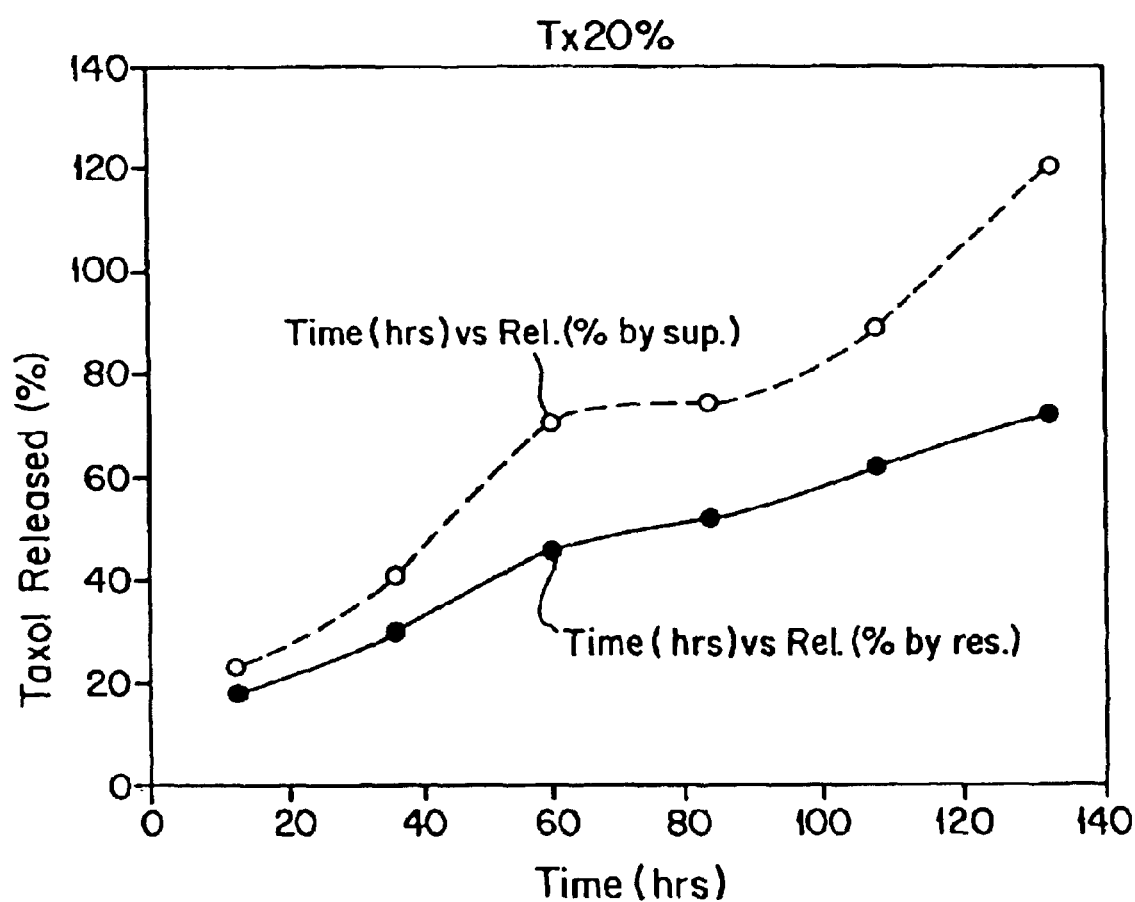
FIG. 4 shows the in vitro release kinetics of taxol/PLGA: 20% core load formulation; Background Specifics; 111 particles; mean=8.15 um; median=3.58 um; Taxol/PLGA Microspheres Counted:132,846; Mean=6.00 um; Median= 3.99 um.
Figure 5:
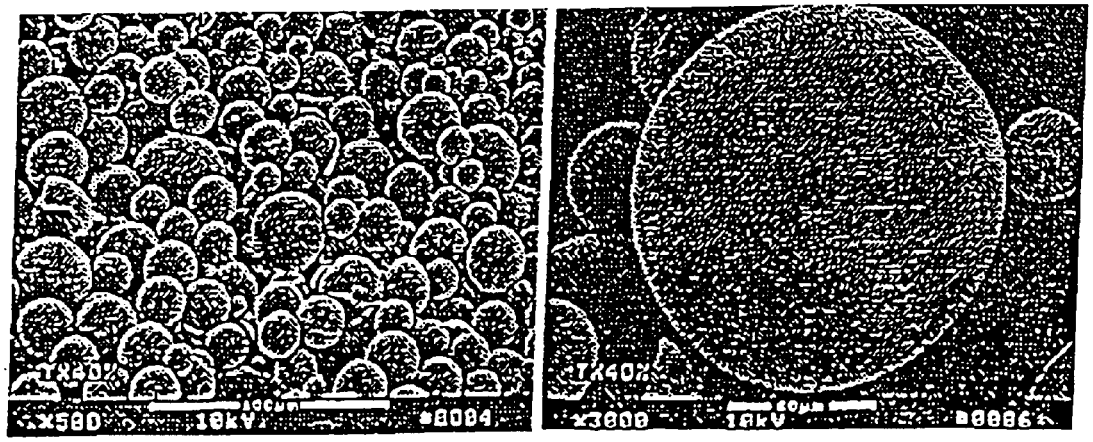
FIG. 5 shows the microsphere morphology of taxol/ PLGA: 40% core load formulation; Background specifics: 171 particles; mean=8.15 um; median=2.46 um; Taxol/ PLGA Microspheres Counted: 116,422; Mean=5.69 um; Median=3.78 um.
Figure 5:
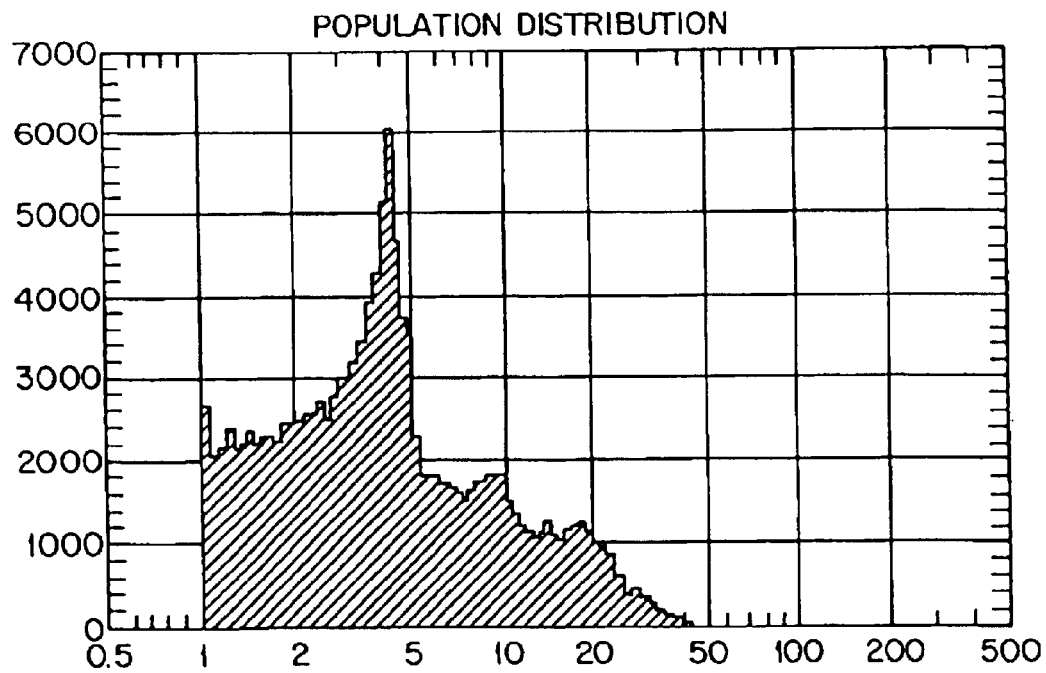
Figure 6:
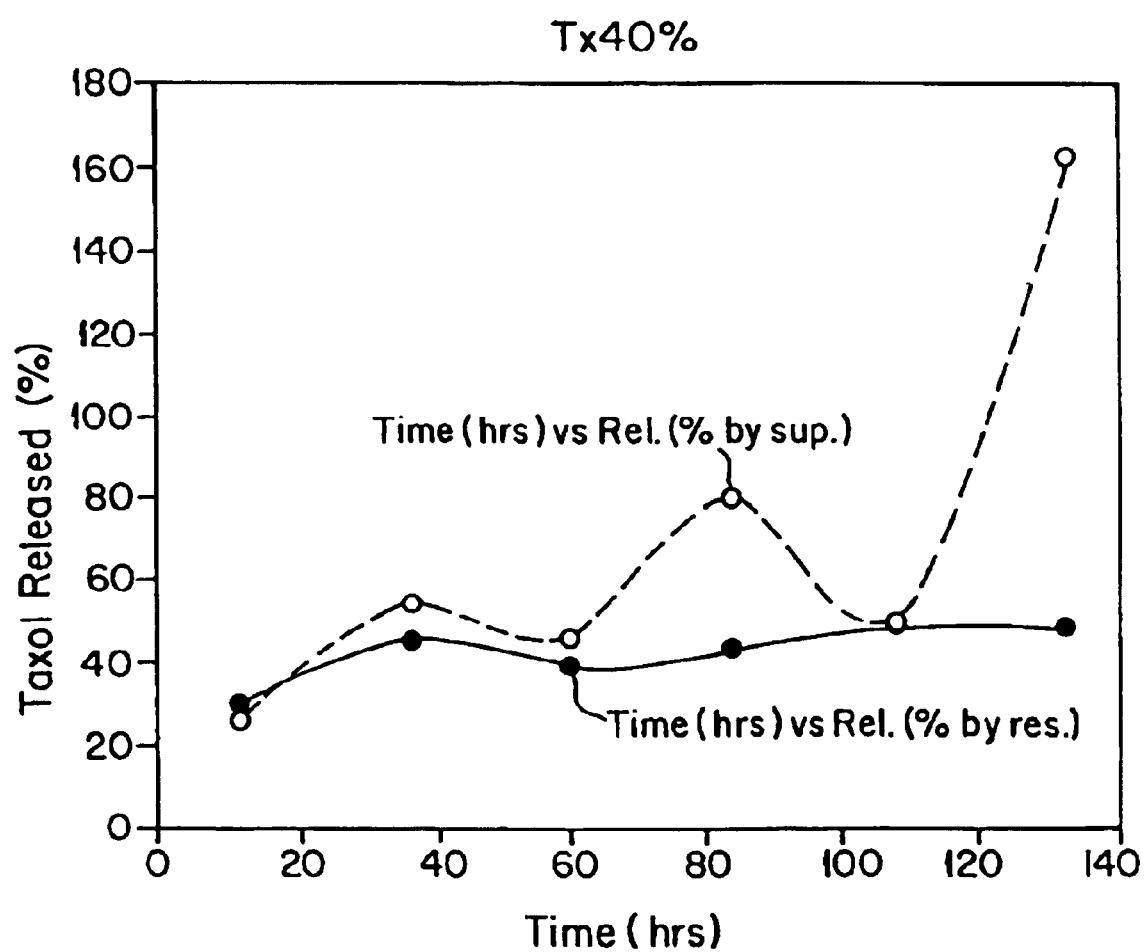
FIG. 6 shows the in vitro release kinetics of taxol/PLGA: 40% core load formulation.
Figure 7:
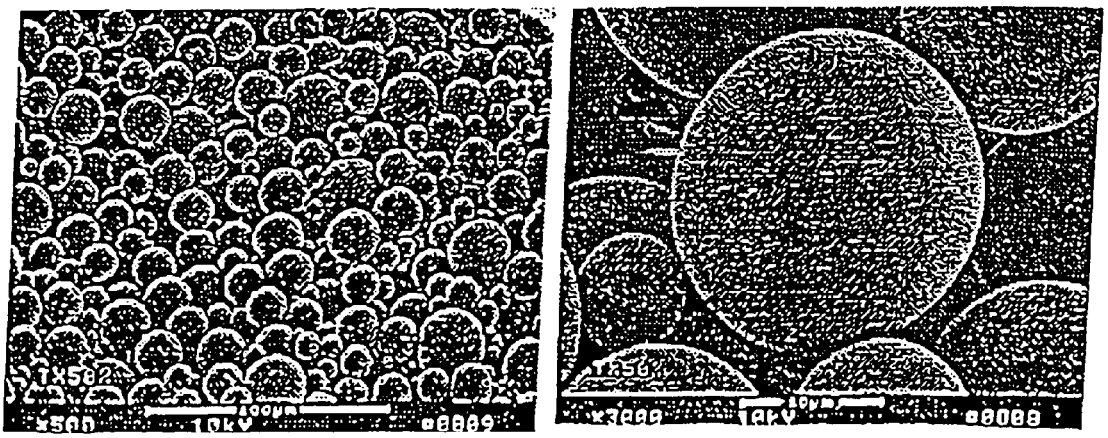
FIG. 7 shows the microsphere morphology of taxol/ PLGA: 50% core load formulation.
Figure 7:
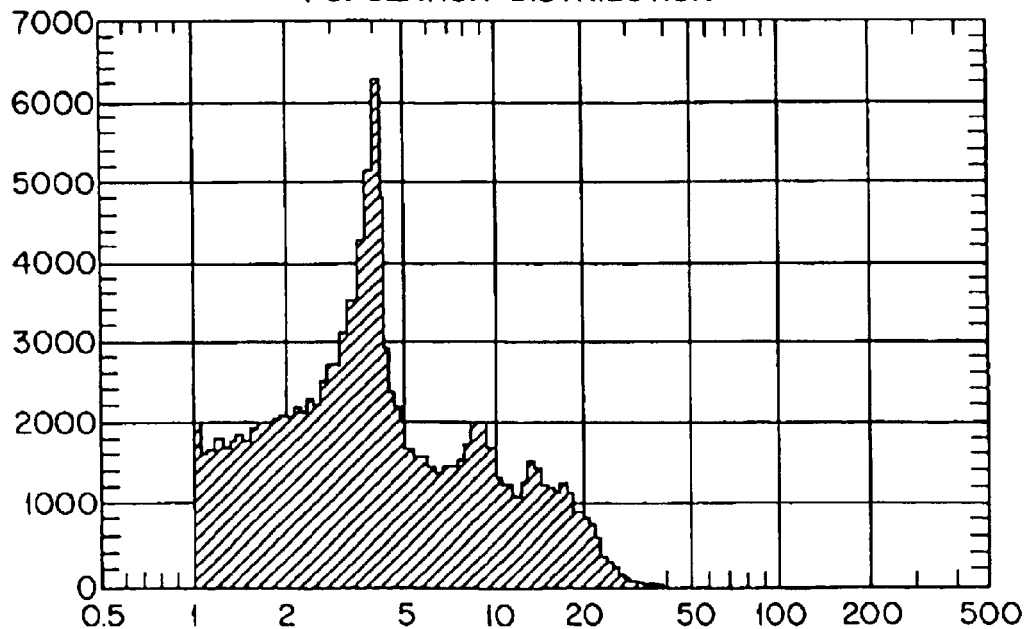
Figure 8:
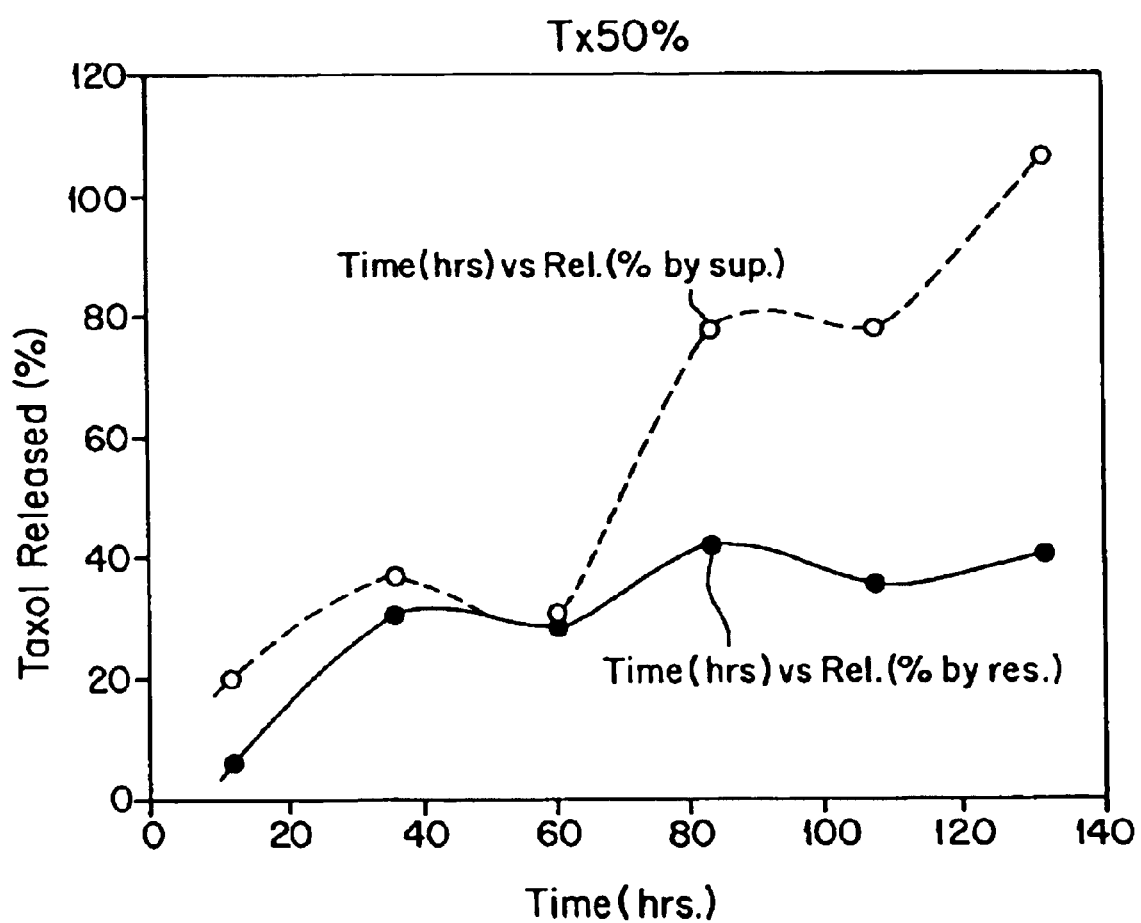
FIG. 8 shows the in vitro release kinetics of taxol/PLGA: 50% core load formulation.

Surprisingly, our data indicates that we have developed a series of taxol/PLGA formulations which exhibit different and highly desirable rates of sustained, controlled release of taxol. Due to the sustained release characteristics of these microspheres, taxol/PLGA microsphere formulations are intended as a one-time treatment which sustain releases taxol from a subcutaneous (s.c) or intramuscular (i.m.) depot. Taxol/PLGA microspheres having a core load of 10%, 20%, 40%, and 50% were prepared via solvent evaporation and were characterized via scanning electron microscopy (SEM), particle sizing, and high performance liquid chromatography (HPLC). Microsphere morphology of these formulations showed intact spheres with an average diameter range of 5.69–7.75 um (FIGS. 1,3,5,7). Taxol core loading efficiency of all formulations ranged form 91.9%–95.48%. In vitro release of taxol into 37 degrees C PMS/albumin (pH 7.4; 0.4% albumin) over time was calculated based on the residual amount of taxol in the microsphere pellet. Results showed: (1)40.19% taxol release in 10 days using a 10% core load formulation; (2) 71.58% taxol release in 6 days using a 20% core load formulation (FIG. 4); (3) 48.09% taxol release in 6 days using a 40% core load formulation (FIG. 6); and (4) 39.84% taxol release in 6 days using a 50% core load formulation (FIG. 8).

A preliminary toxicity study using placebo PLGA microspheres and taxol/PLGA microspheres (20% core load formulation) was performed using C57/black, 6–8 week old, intact female mice. Animals were randomized into 12 groups of 4, ear notched, and weighed. Microencapsulated taxol and control polymer were individually resolubilized and injected either subcutaneously (s.c.) or intramuscularly (i.m. (inocula volume=50 ul). The right side of the animal received control polymer, and the left side of the animal received microencapsulated taxol. Each day, animals were examined for signs of toxicity. On days 2,4,6, and 8, animals were weighed, one from each group was sacrificed, and blood was collected for WBC count and for taxol quantitation via HPLC.

Treatment groups were as follows: (1) dose of 0.04 mg/kg using s.c. route; (2) dose of 0.4 mg/kg using s.c. route; (3) dose of 2 mg/kg using s.c. route; (4) dose of 4 mg/kg using s.c. route; (5) dose of 8 mg/kg using s.c. route; (6) dose of 16 mg/kg using s.c. route; (7) dose of 0.04 mg/kg using i.m. route; (8) dose of 0.4 mg/kg using i.m. route; (9) dose of 2 mg/kg using i.m. route; (10) dose of 4 mg/kg using i.m. route; (11) dose of 8 mg/kg using i.m. route; and (12) dose of 16 mg/kg using i.m. route. Dosage selection was based on the maximum tolerated systemic dose of taxol in mice, which is 16 mg/kg of taxol every 5 days over a 3 week period.

Results showed: (1) no signs of toxicity at the injection sites of any animal at any time; (2) no signs of weight loss rather, on average, the animals gained weight; and (3) no appreciable changes in white blood cell (WBC)count. Taxol concentration in serum samples was too low to be detectable/quantitable via our taxol extraction and HPLC methods. Additionally, problems experienced with the serum samples-were: (1) protein interference with the taxol peak; (2) moderate to gross hemolysis of the serum samples; and (3) the presence of additional peaks in the chromatogram, which may have been taxol metabolites. Further refinement of our methodologies for taxol extraction from serum and for trace HPLC analysis, which is currently in progress, will increase the sensitivity of taxol detection and quantitation and will eliminate these problems. Since no signs of toxicity were determined, this study is being repeated using taxol doses up to 150 mg/kg; however, this preliminary data suggests that depot administration of taxol via microspheres should not cause systemic toxicity.

Applicants have demonstrated that a s.c., or an i.m. injection of taxol encapsulated in a PLGA copolymer is equally as effective as, or perhaps better than, conventional systemic taxol therapy for human breast cancer treatment and does not cause the side effects commonly associated with conventional therapy.

Specific Embodiments

Most specifically, the embodiments of this invention are inclusive of the following items:

1. A controlled release microcapsule pharmaceutical composition of burst-free, sustained, programmable release of a hydrophobic bioactive agent over a duration of 24 hours to 100 days, comprising a hydrophobic bioactive agent and a blend of end-capped and uncapped biocompatible, biodegradable poly(lactide/glycolide).

2. The composition of Item 1 wherein the agent is released in an amount effective to inhibit growth of cancer cells.
3. The composition of Item 2 wherein the biodegradable poly(lactide/glycolide) has ratios ranging from 99/1 to 50/50.
4. The composition of Items 1, 2 or 3 wherein said copolymer has a molecular weight from 10 to 100 kDa.
5. The composition of Items 1, 2, 3 or 4 wherein the copolymer is a blend of hydrophobic end-capped polymer with terminal residues functionalized as esters and hydrophillic uncapped polymer with terminal residues existing as carboxylic acids.
6. The composition of Items 1, 2, 3, 4, or 5 wherein the agent is selected from the group consisting of paclitaxel, doxorubicin, 5-fluorouracil, camptothecin, cisplatin, metronidazole, and combinations thereof.
7. The compositions of Items 1, 2, 3, 4, 5 or 6 further comprising additional biologically active compounds selected from the group consisting of chemotherapeutics, antibiotics, antivirals, antinflammatories, cytokines, immunotoxins, anti-tumor antibodies, anti-angiogenic agents, anti-edema agents, radiosensitizers, and combinations thereof.
8. A method of administering to a patient in need of treatment a pharmaceutically-effective amount of a hydrophobic bioactive agent comprising administering the bioactive agent locally to an infectious area, wherein the agent is incorporated into and controlled released, burst-free, from a blend of end-capped and uncapped biocompatible, biodegradable poly(lactide/glycolide) over a period of 24 hours to 100 days.
9. The method of Item 8 wherein the bioactive agent is an anticancer agent.
10. The method of Item 9 wherein the anticancer agent is selected from the group consisting of paclitaxol, doxorubicin, 5-fluorouracil, camptothecin, cisplatin, metronidazole, and combinations thereof.
11. The method of Item 10 wherein the anticancer agent is paclitaxol.
12. The method of Item 8, 9, 10 or 11 wherein the bioactive agent is administered to the patient prior to the onset of infections.
13. The method of Item 8, 9, 10 or 11 wherein the bioactive agent is administered to the patient in need thereof post-infection.
14. The method of Item 8, 9, 10 or 11 wherein the bioactive agent is administered intra-muscularly or subcutaneously.
15. The method of Item 8 further comprising administering radiation in combination with the composition.
16. The method of Item 8 further comprising administering with the bioactive agent additional biologically active compounds selected from the group consisting of chemotherapeutics, antibiotics, antivirals, antiinflammatories, cytokines, immunotoxins, antitumor antibodies, anti-angiogenic agents, anti-edema agents, radiosensitizers, and combinations thereof.
17. The method of Item 8 wherein the composition is in the form of micro-implants and are administered by injection or infusion.
18. The method of Item 10 wherein the form of cancer being treated is selected from the group consisting of ovarian, breast, lung, prostatic, and melanoma, brain tumor cells, and cancer of the colon-rectum, esophagus, liver, pancreas, and kidney.
19. A method for inhibiting the proliferation of rapidly proliferating abnormal mammalian cells, said method comprising contacting said cells with a cell proliferating inhibiting amount of an anticancer agent which has been incorporated into and controlled released, burst-free, from a blend of end-capped and uncapped biocompatible, biodegradable poly(lactide/glycolide), for a programmable time sufficient to inhibit said proliferation.

EXAMPLES

The following examples are offered by way of illustration and not by way of limitation.

Experimental

The abbreviations used herein are defined as follows:

A) Acronym and Symbol Definition

Figure 2:
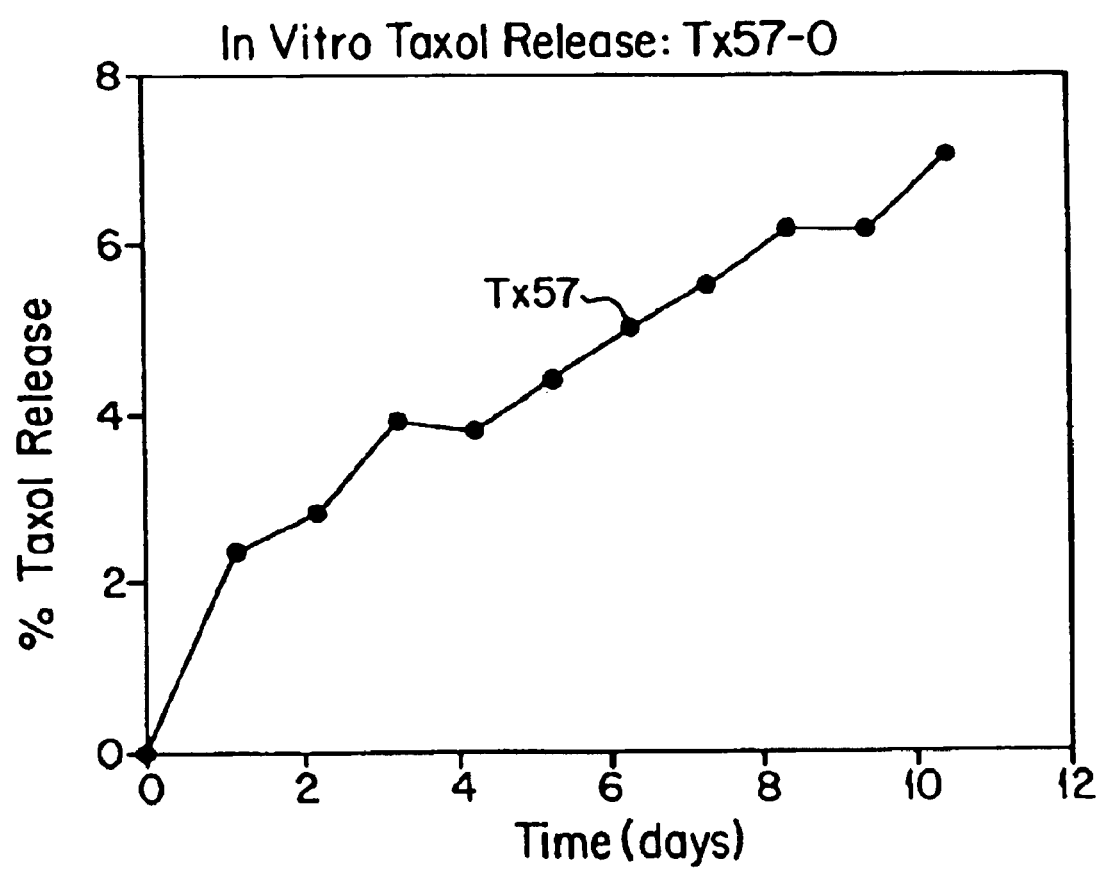
FIG. 2 shows the in vitro release kinetics of taxol/PLGA: 10% core load formation; Summary of Taxol Release; (1) Amount of taxol released over 10 days (based on supernatant data)=7.06% (749.13 ug). (2) Amount of taxol released over 10 days (based on residual data); Residual Taxol at 10 days=59.81% (6350.5 ug); 100%−59.81%=40.19% released over 10 days. (3) Time for complete PLGA degradation= approximately 20 days.
Figure 3:
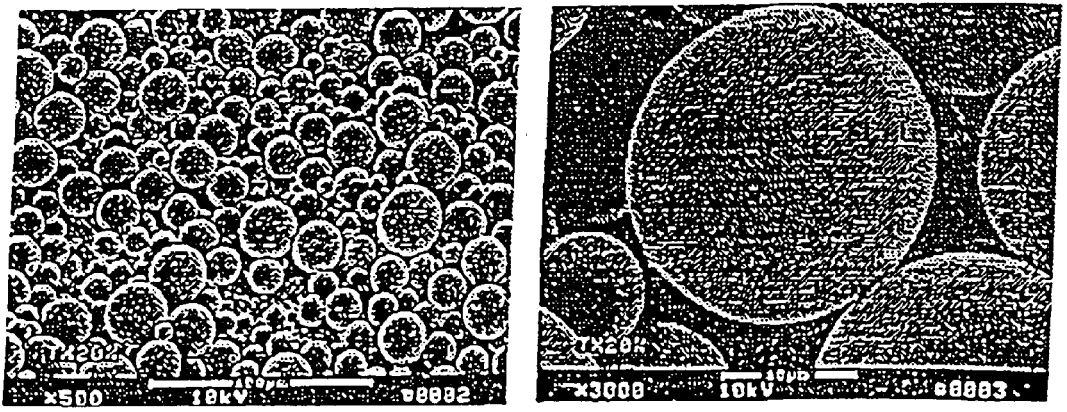
FIG. 3 shows the microsphere morphology of taxol/ PLGA: 20% core load formulation; Background Count Specifics; 103 particles; mean=3.39 um; median=1.78 um; Taxol/PLGA Microspheres Counted: 84,768; Mean=6.43 um; Median=4.69 um.
Figure 3:
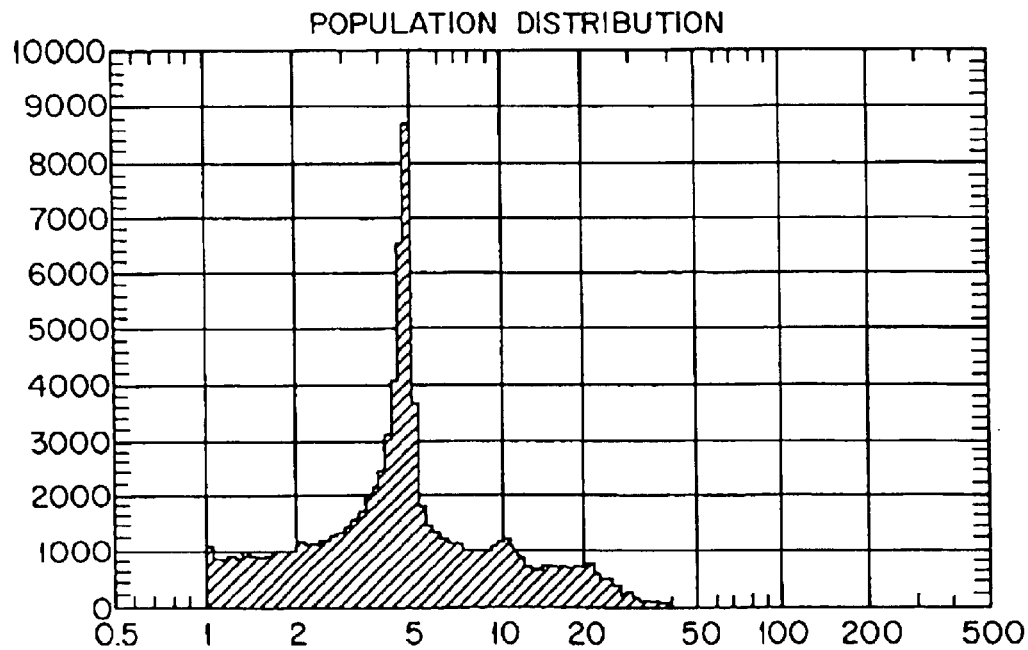

ABC=3 amino-9-ethylcarbazole
CRDA=collaborative research and development agreement
CT=Chemotherapy
HPLC=HIGH PERFORMANCE LIQUID CHROMATOGRAPHY
i.v.=Intra-venous
i.p.=Intrapariteneal
i.m.=Intra-muscular
MDR=Multi-drug resistant
PBS=Phosphate-buffered saline
PLGA=Poly(lactide-co-glycolide)
s.c.=Subcutaneous
SEM=Scanning electron microscope Materials and Method Preliminary Results: Paclitaxel (taxol) is being used as the prototype hydrophobic drug for the development of a PLGA copolymer delivery vehicle for hydrophobic drugs. Paclitaxel is a diterpene anticancer agent isolated from the bark of the Western Pacific yew, Taxus brevifolia (FIG. 2) (3). Taxol binds intracellular microtubules, adversely affecting functions critical to cell mitosis via promotion of abnormal microtubule formation and via stabilization of formed microtubules (4,5). Taxol exhibits non-linear pharmacokinetics, in that there is a disproportionate relationship between changes in dose and resulting peak plasma concentrations (6). Taxol use is indicated for the treatment of human breast cancer after failure of combination CT for metastatic disease or upon disease relapse within 6 months of adjuvant CT.

PHASE I. Validation of Methodology for paclitaxel analysis.

A. Accuracy/Precision

1. Experimental Set Up: A 5.0 ug/ml paclitaxel solution was run 10 times, and the relative standard deviation percent (RSD%) was calculated. This validation step was performed on both HPLC instruments at U.S. Army Dental Research Attachment, Walter Reed Institute of Research (USADRD-WRAIR).

2. Result: The RSD% of System 1 was 1.2131, and the RSDZ of the Waters Modular System was 1.592.

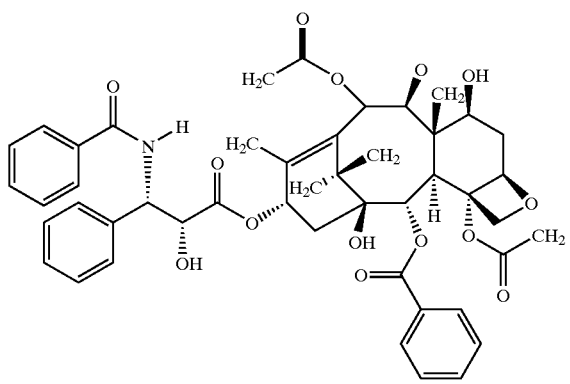

CHEMICAL FORMULA FOR PACLITAXEL(taxol)

B. Detection/Quantitation Limit and Linearity
1. Detection Limit:
  a. Experimental Set-Up: A 0.5 ug/ml taxol solution was serially diluted to 0.015625 ug/ml. The peak to noise ratio was examined to determine the detection limit of each HPLC system.
  b. Result: The detection limit of both HPLC systems was 0.015625 ug/ml.
2. Quantitation Limit/Linearity
  a. Experimental Set-Up: 30 calibration curves from each HPLC run are being collected for subsequent analysis.

C. Recovery
1. Experimental Set-Up: A known amount of paclitaxel was added to PBS/albumin (the paclitaxel release buffer), and a liquid-liquid extraction of paclitaxel was performed. The concentration of paclitaxel after extraction was compared to the expected paclitaxel concentration to verify the efficiency of the extraction methodology.
2. Result: Average percent recovery of paclitaxel after liquid-liquid extraction was 98%.

D. Sample Solution Stability in PBS/Albumin
1. Experimental Set-Up: The stability of paclitaxel in PBS/albumin was determined over a 6 day period. 4 separate paclitaxel containing samples were followed over a 6 day period.
2. Result: Average paclitaxel concentration of each sample was calculated by pooling the 6 days of HPLC data.
  a. Paclitaxel concentration of sample 1: 1.6344+/−0.2895
  b. Paclitaxel concentration of sample 2: 0.053+/−0.002915
  c. Paclitaxel concentration of sample 3: 0.0482+/−0.001924
  d. Paclitaxel concentration of sample 4: 0.0545+/−0.003017

E. Specificity/Selectivity
1. Acid/Base Hydrolysis of Paclitaxel
  a. Experimental Set-Up: A 20 ug/ml paclitaxel solution was exposed to PBS/albumin at the following pH's: 7.4, 10.0, and 2.0. Following a 72 hour exposure, a liquid-liquid extraction of paclitaxel was performed.
  b. Result: Acid conditions did not have an effect on paclitaxel, but basic conditions resulted in paclitaxel degradation.
2. Effect of DH on Paclitaxel Retention
  a. Experimental Set-Up: Mobile phase pH and corresponding paclitaxel retention time specifics are being recorded after every HPLC run.

F. Robustness
1. Experimental Set-Up: 30 calibration curves from each HPLC run are being collected for subsequent analysis.

G. Effect of Irradiation on Paclitaxex
1. Experimental Set-Up: A 15 mg sample of paclitaxel powder was irradiated with 20.7–21.4 kGy, a radiation level 10% greater than the standard 20 kGy target. A comparison between the paclitaxel peak of the irradiated sample was compared to that of an unirradiated sample.
2. Result: Gamma irradiation did not affect the paclitaxel peak.

H. Comparison Between Liquid/Liquid and Solid Phase Extraction
1. Experimental Set Up: Liquid/liquid extraction of paclitaxel is highly time-consuming and labor intensive, therefore, an alternative method for paclitaxel extraction, solid phase extraction, was recently examined in terms of extraction efficiency. Liquid/liquid extraction and solid phase extraction were performed on 3 separate 2 ug/ml paclitaxel solutions.
2. Result: Area comparisons were follows:
  a. 2 ug/ml paclitaxel solution (no extraction): 52,230+/−3,244
  b. 2 ug/ml paclitaxel solution (liquid/liquid extraction): 48,648+/−2,571
  c. 2 ug/ml paclitalex solution solid phase extraction): 59,346+/−4,962
  d. Solid phase extraction of paclitaxel will replace liquid/liquid extraction of paclitaxel.

I. Photodiode Array (PDA) Detection of Paclitaxel
1. Experimental Set-Up: A paclitaxel standard in acetonitrile/d. water was prepared and run through the PDA detector. This result was used for the Millennium's PDA spectrum purity analysis as the reference spectra to compare against 3 in vitro samples, extracted by liquid/liquid extraction, containing a known amount of paclitaxel. The purity and the threshold angle between the paclitaxel samples and the paclitaxel standard were calculated. These calculated numbers correspond to the purity of the paclitaxel peak that is being analyzed via paclitaxel's HPLC methodology.
2. Result: For each comparison, the purity angle was less than the threshold angle, indicating that the paclitaxel peak being analyzed via HPLC is pure.

PHASE II: Production and Analysis of Paclitaxel/PLGA Microspheres
  A. Preliminary Screening of Paclitaxel/PLGA Microsheres
    1. Purpose: Preliminary screen of a series of paclitaxel microspheres produced using a variety of PLGA copolymers and of external phase stir rates.
      a. Copolymers Examined:
        High Molecular Weight PLGA: RG504, a non-H series copolymer, and RG504H, an H-series copolymer.
        Low Molecular Weight PLGA: RG502 and RG502H
Rationale for Screening Different Molecular Weight Copolymers: As the molecular weight of the copolymer decreases, drug release rate increases.
Rationale for Screening H vs. Non-H Series Copolymers: H-series copolymers hydrate faster than the non-H series copolymers due to the presence of carboxylic acid end chains. Quicker hydration of the copolymer results in an accelerated drug release rate.
      b. External Phase Stir Rates Examined: 250, 500, and 960 rpm.
Rationale for Examining Different Stir Rates: As the stir rate increases, smaller microspheres result in an accelerated drug release rate.

2. Result a. Paclitaxel Core Loads Paclitaxel-loaded microspheres were dissolved in acetonitrile/d. water and then run on the HPLC against a set of paclitaxel-containing standards (Table 1).

| Formulation | Stir Rate (rpm) | Paclitaxel (ug/ml) | % Core Load CL | % Theoretcial CL | % Loading Efficiency | Paclitaxel Mg | PLGA, mg and Type |
|---|---|---|---|---|---|---|---|
| Tx03 | 250 | 45.388 | 4.407 | 5 | 88.131 | 10 | 190RG504 |
| Tx04 | 250 | 97.905 | 9.324 | 10 | 93.243 | 20 | 180RG504 |
| Tx05 | 250 | 176.104 | 16.772 | 20 | 83.859 | 40 | 160RG104 |
| Tx07 | 960 | 96.407 | 9.010 | 10 | 90.100 | 20 | 180RG504 |
| Tx08 | 960 | 166.076 | 15.969 | 20 | 79.844 | 40 | 160RG504 |
| Tx09 | 960 | 100.628 | 9.676 | 10 | 96.758 | 20 | 180RG504H |
| Tx10 | 960 | 185.829 | 17.206 | 20 | 86.032 | 40 | 160RG504H |
| Tx11 | 960 | 91.340 | 8.955 | 10 | 89.549 | 20 | 180RG502 |
| Tx12 | 960 | 173.742 | 16.706 | 20 | 83.530 | 40 | 160RG502 |
| Tx13 | 500 | 85.137 | 8.108 | 9.090 | 89.191 | 20 | 200RG504 |
| Tx14 | 500 | 144.042 | 13.850 | 16.667 | 83.101 | 40 | 200RG504 |
| Tx15 | 500 | 83.251 | 7.929 | 9.090 | 87.215 | 20 | 200RG504H |
| Tx16 | 500 | 153.061 | 14.717 | 16.667 | 88.304 | 40 | 200RG504H |
| Tx17 | 500 | 89.999 | 8.490 | 9.090 | 93.395 | 20 | 200RG502 |
| Tx18 | 500 | 157.295 | 14.700 | 16.667 | 88.203 | 40 | 200RG502 |
| Tx19 | 250 | 82.756 | 7.882 | 10 | 78.815 | 20 | 180RG504 |
| Tx20 | 250 | 163.937 | 16.394 | 20 | 81.969 | 40 | 160RG504 |
| Tx21 | 250 | 75.590 | 7.268 | 10 | 72.683 | 20 | 180RG504H |
| Tx22 | 250 | 172.609 | 16.439 | 20 | 82.195 | 40 | 160RG504H |
| Tx23 | 250 | 87.821 | 8.364 | 10 | 83.639 | 20 | 180RG502H |
| Tx24 | 250 | 168.144 | 16.168 | 20 | 80.838 | 40 | 160RG502 |
| Tx25 | 960 | 100.522 | 9.573 | 10 | 95.735 | 20 | 180RG503 |
| Tx26 | 960 | 194.583 | 18.710 | 20 | 93.550 | 40 | 160RG503 |
| Tx27 | 960 | 95.110 | 9.324 | 10 | 93.245 | 20 | 180RG503H |
| Tx28 | 960 | 185.929 | 18.593 | 20 | 92.965 | 40 | 160RG503H |
| Tx29 | 960 | 103.769 | 10.173 | 10 | 101.734 | 20 | 180RG502H |
| Tx30 | 960 | 191.514 | 18.415 | 20 | 92.074 | 40 | 160RG502H |
| Tx31 | 500 | 90.823 | 8.992 | 10 | 89.924 | 20 | 180RG503 |
| Tx32 | 500 | 183.843 | 17.849 | 20 | 89.244 | 40 | 160RG503 |
| Tx33 | 500 | 97.025 | 9.240 | 10 | 92.405 | 20 | 180RG503 |
| Tx34 | 500 | 193.375 | 18.417 | 20 | 92.083 | 40 | 160RG503H |
| Tx35 | 500 | 97.559 | 9.565 | 10 | 95.646 | 20 | 180RG502H |
| Tx36 | 500 | 190.431 | 18.488 | 20 | 92.442 | 40 | 160RG502H |
| Tx37 | 250 | 90.497 | 8.872 | 10 | 88.723 | 20 | 180RG503 |
| Tx38 | 250 | 151.375 | 14.841 | 20 | 74.203 | 40 | 160RG503 |
| Tx39 | 250 | 94.872 | 9.211 | 10 | 92.108 | 20 | 180RG503H |
| Tx40 | 250 | 193.068 | 19.307 | 20 | 96.534 | 40 | 160RG503H |
| Tx41 | 250 | 100.750 | 9.782 | 10 | 97.816 | 20 | 180RG502H |
| Tx42 | 250 | 180.313 | 18.031 | 20 | 90.157 | 40 | 160RG502H |

Paclitaxel Loading Efficiency: 72–96% b. Scanning Electron Microscope Results:

The morphology of paclitaxel-loaded microspheres was examined via SRM.

RG504 Copolymer: Intact microspheres, with an average diameter of 100 um.

RG504H Copolymer: Intact microspheres, with an average diameter of 100 um.

RG503 Copolymer: Intact microspheres, with an average diameter of 100 um. Morphologic damage, including cracked, misshapen, hollow, and dented microspheres, was noted.

RG503H: Intact microspheres, with an average diameter of 100 um. Morphologic damage was noted.

RH502: No intact microspheres were present.

RG502H: No intact microspheres were present.

c. In vitro Paclitaxel Release

Experimental Set-Up: 10 mg of paclitaxel-loaded microspheres were suspended in 50 ml PBS/albumin (0.2% mass) and placed in a 37 degree Celsius shaking water bath. At specified time intervals, 48 ml of the supernatant was removed for subsequent HPLC analysis and the sample was replenished with 48 ml of fresh buffer. The 50 ml volume and the timing of the sampling ensure that sink conditions are met.

Figure 11:
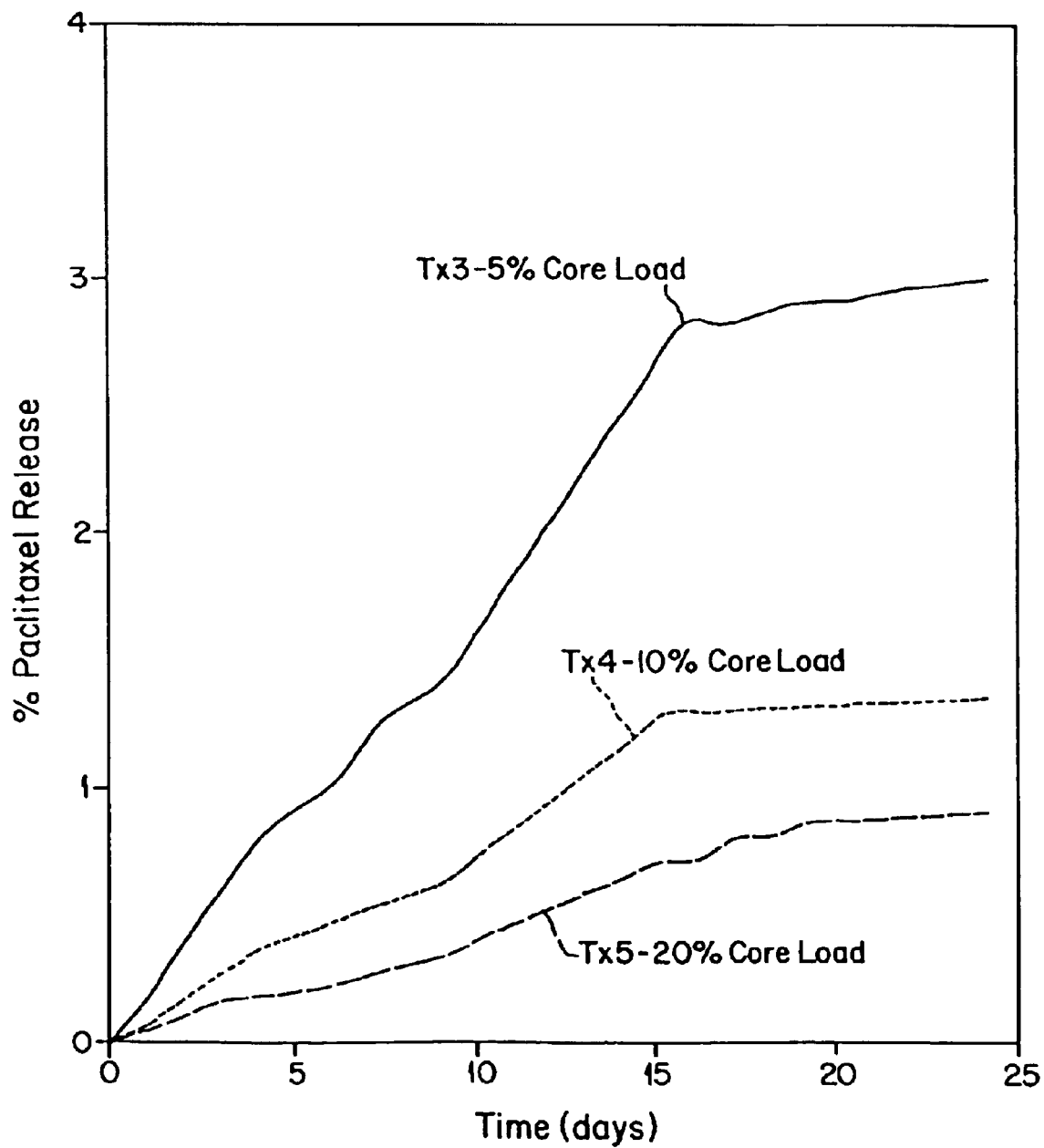
FIG. 11 shows the in vitro paclitaxel release from Tx3, Tx4 and Tx5.
Figure 12:
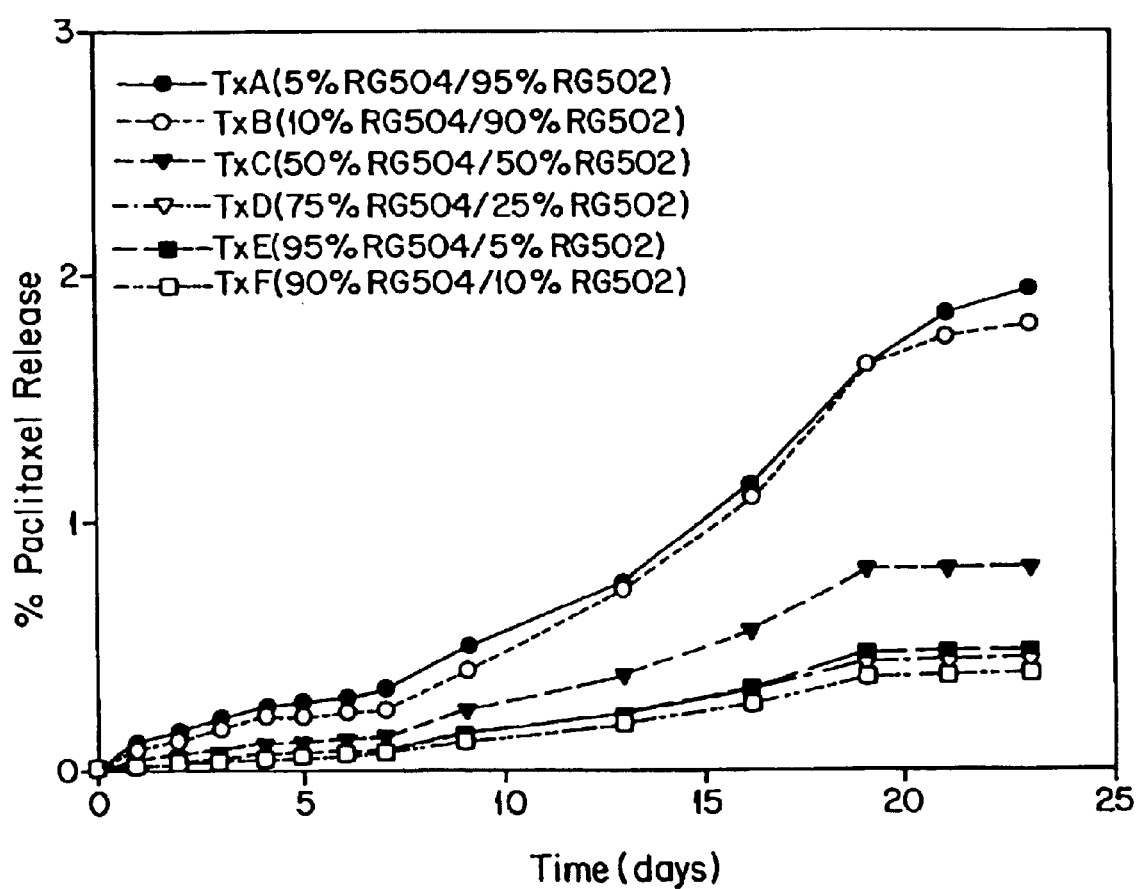
FIG. 12 shows the in vitro paclitaxel release from RG504/ RG502 blends.
Figure 13:
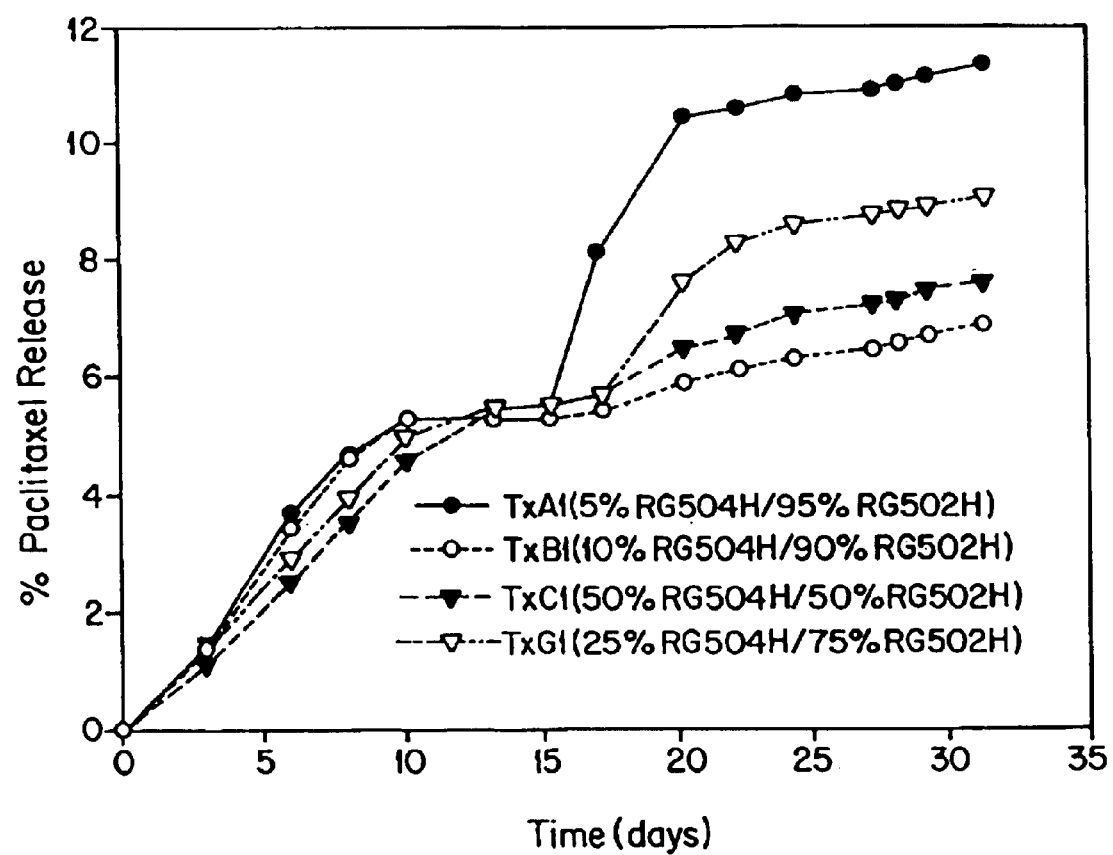
FIG. 13 shows the in vitro paclitaxel release from RG504H/RG502H blends.
Figure 14:
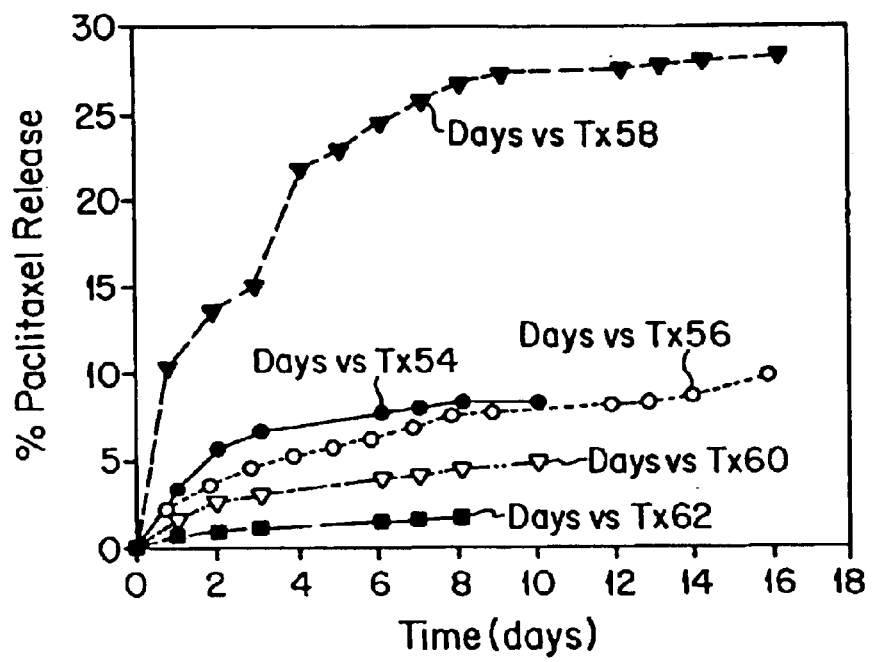
FIG. 14 shows the in vitro paclitaxel release from non-H series copolymer blends.
Figure 15:
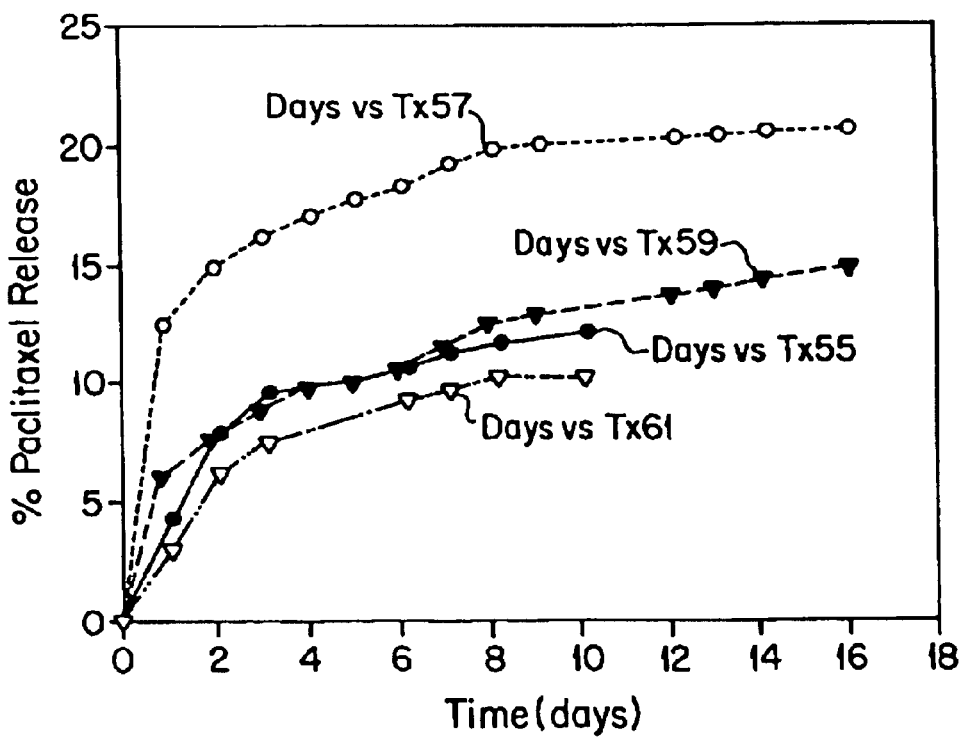
FIG. 15 shows the in vitro paclitaxel release from H series copolymer blend.
Figure 16:
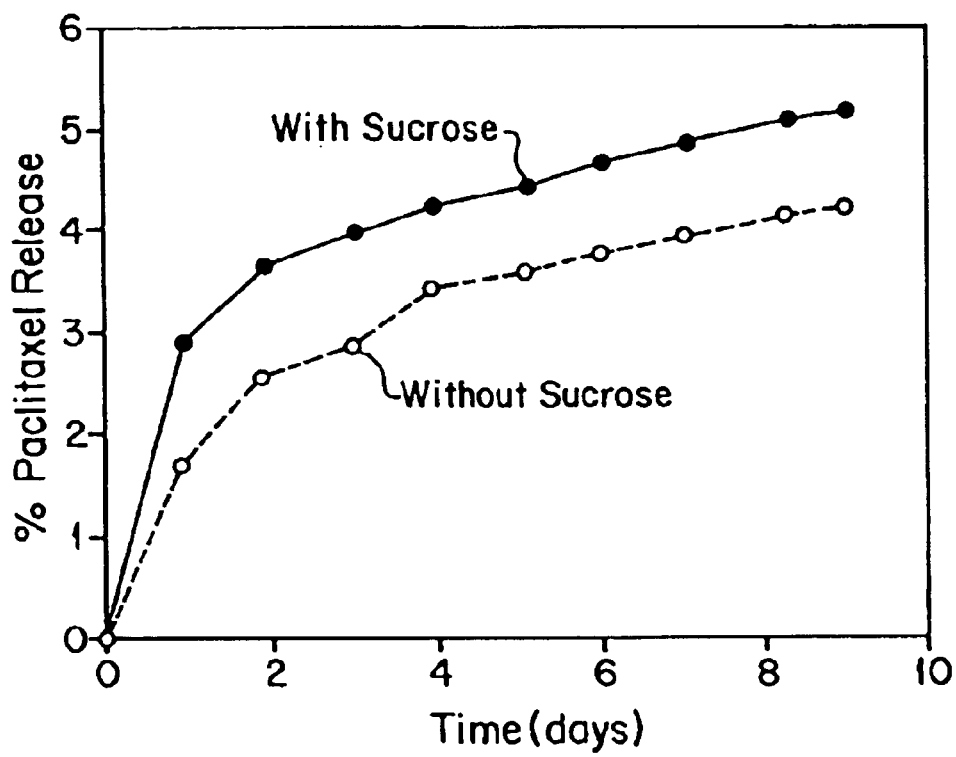
FIG. 16 shows the in vitro paclitaxel release in the presence of sucrose in the PLGA matrix.
Figure 17:
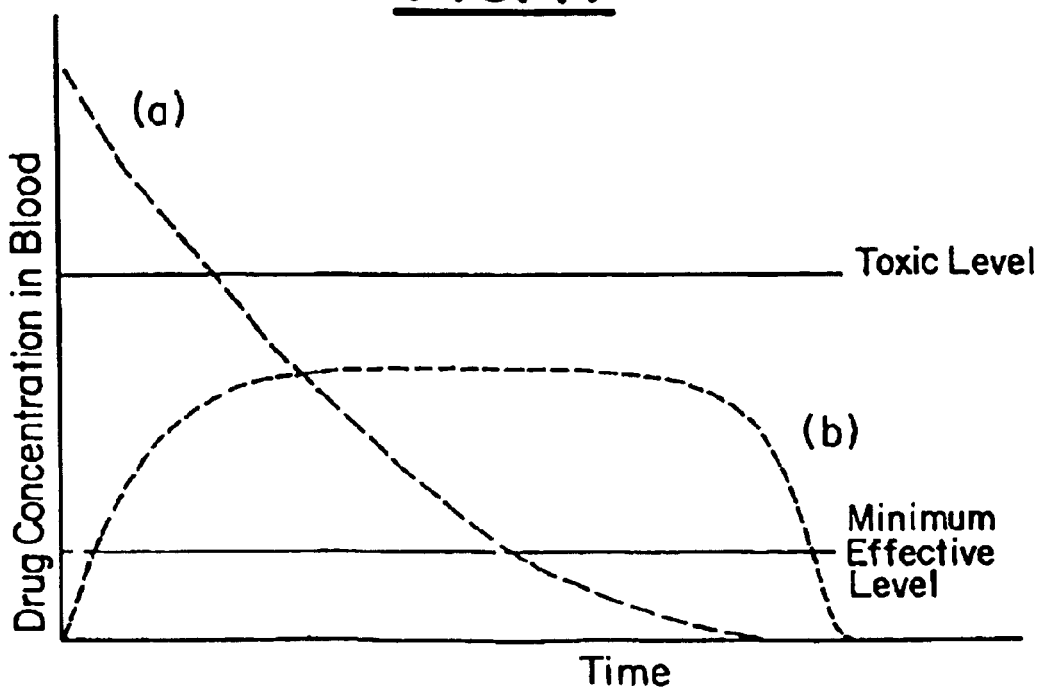
FIG. 17 shows the theoretical plasma concentrations after administration of dosage forms: (a) intraveous(i.v.) administration and (b) controlled release system.
Figure 18:
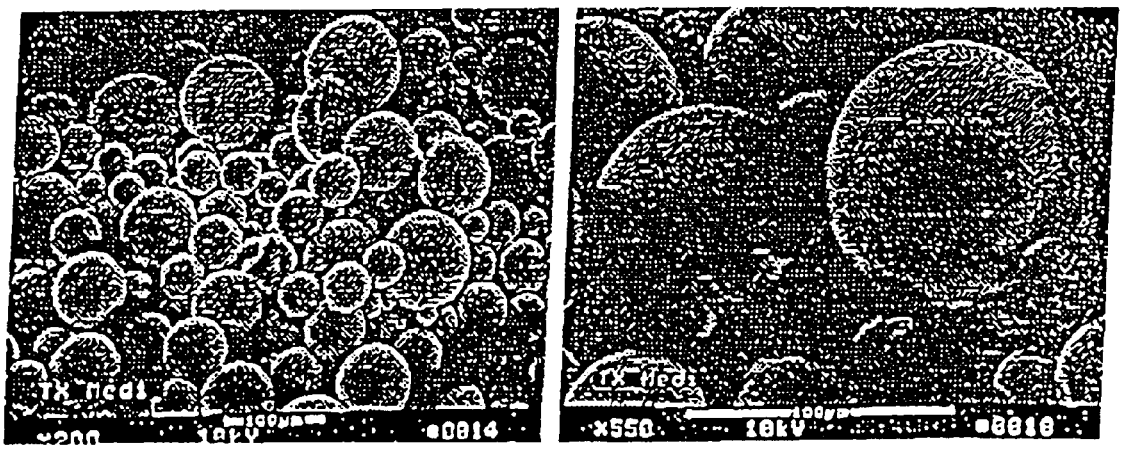
FIG. 18 shows the microsphere morphology of taxol/ PLGA: TX Medisorb formulation; Background Count Specifies: 392 particles; mean=6.33 um; median.
Figure 18:
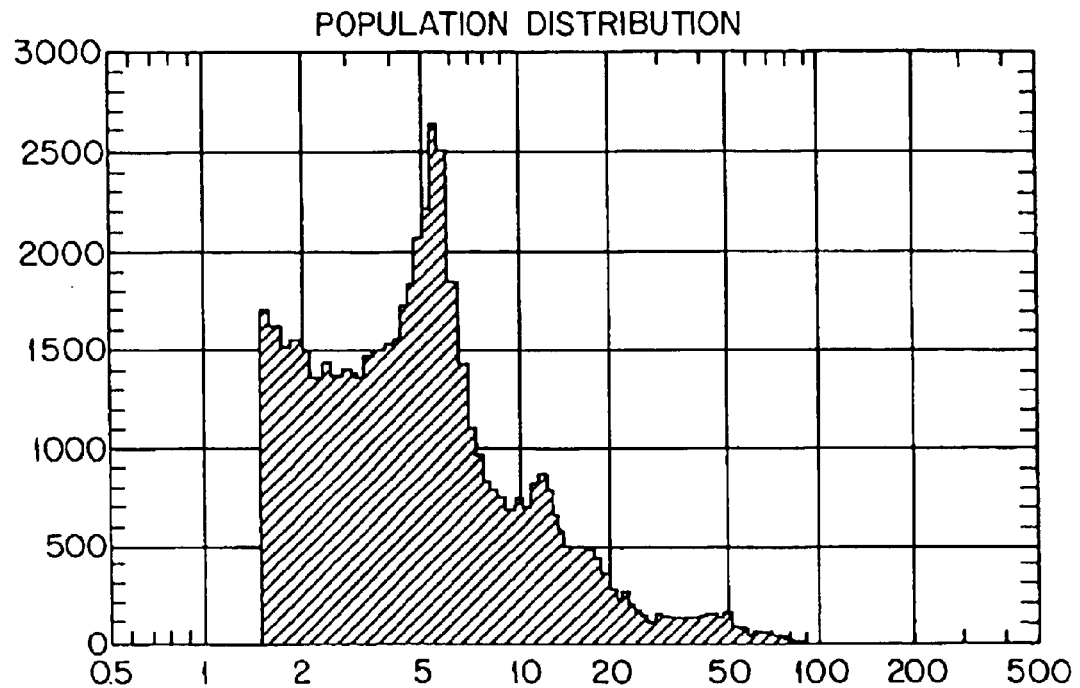
Figure 19:
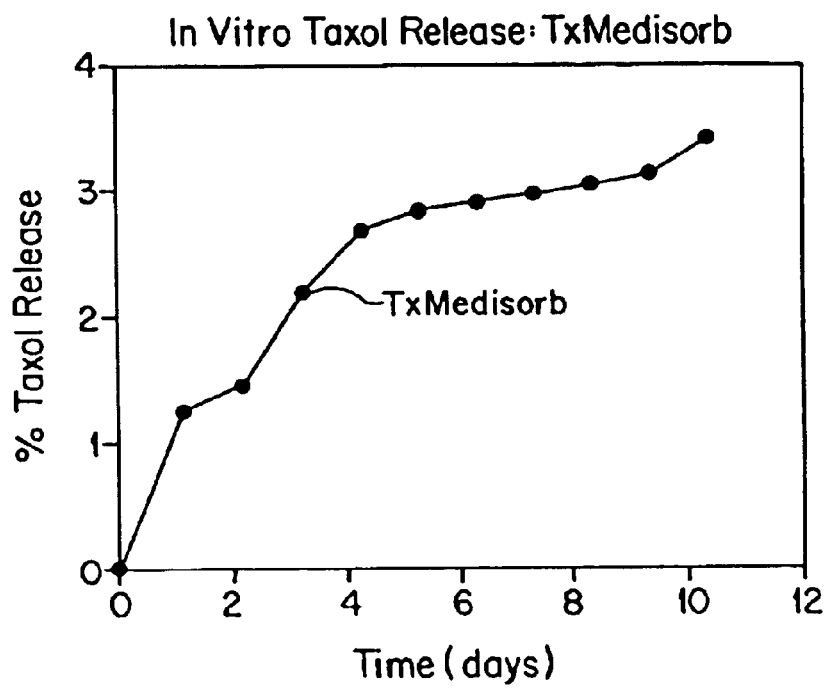
FIG. 19 shows the in vitro release kinetics of taxol/PLGA: TX Medisorb formulation; Summary of Taxol Release; (1) Amount of taxol released over 10 days (based on supernatant data)=3.41% (308.095 ug); (2) Amount of taxol released over 10 (based on residual data) 100%−36.13%=63.8% released over 10 days; (3) Time for complete PLGA degradation=approximately 60–80-days.
Figure 20:
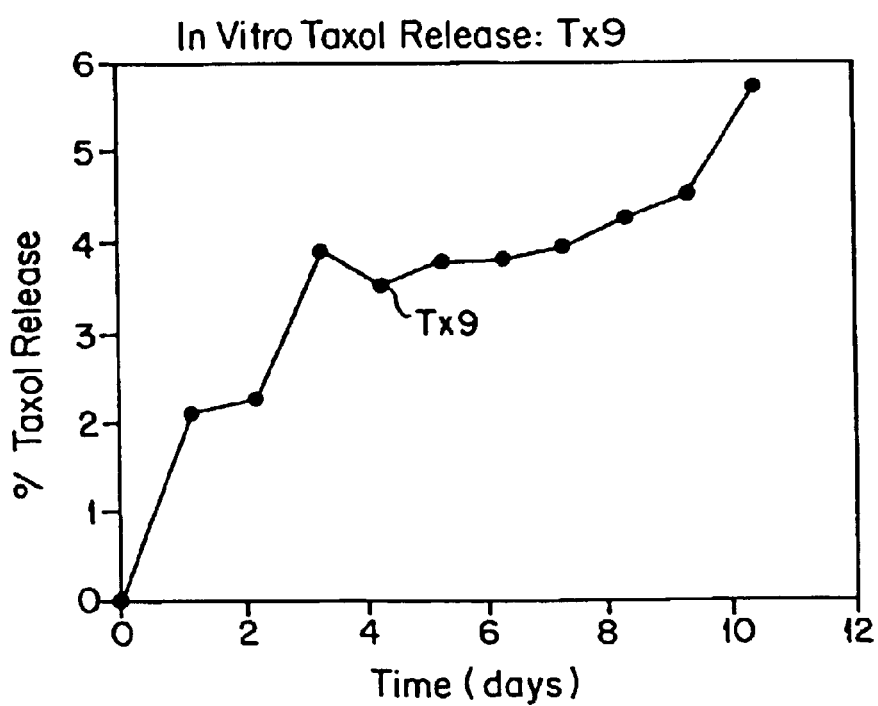
FIG. 20 shows the in vitro release kinetics of taxol/PLGA: Tx9 formulation; Summary of Taxol Release; (1) Amount of taxol released over 10 days (based on supernatant data)= 5.70% (525.135 ug); (2) Amount of taxol released over 10 days (based on residual data) Residual taxol at 10 days= 67.3% (6207.5 ug) 100 %−67.36%=32.64% released over 10 days; degradation=(3) Time for complete PLGA approximately 30–60 days.

In vitro Paclitaxel Release From Formulations Tx3. Tx4. and Tx5 (FIG. 11):

(a) Paclitaxel-loaded microspheres containing RG503 (non-H and H) and RG502(non-H and H), as opposed to those containing RG504(non-H and H), showed structural damage; therefore, only RG504(non-H and H) containing microspheres were selected for subsequent analysis.

(b) All formulations which consisted of intact, undamaged microspheres averaged microsphere diameters of 100 um; therefore, a subset of these formulations, Tx3, Tx4, and Tx5, were selected for subsequent release analysis.

3. Conclusions a. Paclitaxel was efficiently encapsulated in PLGA using solvent evaporation methodology.

b. As the molecular weight of the polymer decreased, paclitaxel-loaded microspheres lost structural stability.

c. The stir rate effect, in terms of microsphere size, was not highly evident due to the molecular weight of the copolymer. Using high molecular weight copolymer, RG504 and RG504H, resulted in large microspheres regardless of the applied external phase stir rate.

d. Paclitaxel release from RG504 was slow due to the large size of the microspheres.

B. Paclitaxel Formulations Consisting of RG504 (non-H and H)/RG502 9non-H and H) Blends 1. Purpose and Rationale: To improve the structural stability of RG502(non-H and H)-containing paclitaxel microspheres and to increase the paclitaxel release rate via blending RG504(non-H and H), the high molecular weight copolymer, with RG502(non-H and H), the low molecular weight copolymer. The rationale for this approach is that RG504(non-H and H) will provide structural stability to the microsphere and that RG502(non-H and H) will allow for faster hydration of the microspheres. Faster hydration results in accelerated drug release.

2. System Parameters Examined: Combinations of either RG504 and RG502 or RG504H and RG502H. External phase stir rate was held constant at 1000 rpm in order to determine the effect of microsphere composition, in terms of the ratio of RG504(non-H and H) to RG502(non-H and H), upon paclitaxel release.

TABLE 2

Paclitaxel Core Loads

| Formulation | Paclitaxel (ug/ml) | % Core Load | % Theoretical CL | % loading efficiency | Paclitaxel, mg | PLGA, mg and type |
|---|---|---|---|---|---|---|
| A | 104.742 | 9.88 | 10 | 96.814 | 20 | 180 5% RG504/95% RG502 |
| B | 84.414 | 8.441 | 10 | 84.415 | 20 | 180 10% RG504/90% RG502 |
| C | 94.004 | 8.953 | 10 | 89.528 | 20 | 180 50% RB504/50% RG502 |
| D | 100.560 | 9.866 | 10 | 98.656 | 20 | 180 75% RG504/25% RG502 |
| E | 93.288 | 9.057 | 10 | 90.570 | 20 | 180 95% RG504/5% RG502 |
| F | 100.667 | 9.680 | 10 | 96.795 | 20 | 180 90% RG504/10% RG502 |
| G | 89.189 | 8.494 | 10 | 84.941 | 20 | 180 25% RG504/75% RG502 |
| A1 | 95.627 | 9.375 | 10 | 93.752 | 20 | 180 5% RG504H/95% RG502H |
| B1 | 92.768 | 9.185 | 10 | 91.849 | 20 | 180 10% RG504H/90% RG502H |
| C1 | 100.761 | 9.763 | 10 | 97.826 | 20 | 180 |
| D1 | 104.187 | 10.018 | 10 | 100.018 | 20 | 180 50% RG504H/50% RG502H |
| E1 | 93.277 | 9.235 | 10 | 92.353 | 20 | 180 95% RG504H/%5% RG502H |
| F1 | 92.469 | 9.249 | 10 | 92.480 | 20 | 180 90% RG504H/10% RG502H |
| G1 | 96.491 | 9.849 | 10 | 96.491 | 20 | 180 25% RG504H/75% RG502H |

Paclitaxel Loading Efficiency: 84–99% b. SEM Results:

RG504/RG502 Blends:

TxA: Intact microspheres, with an average diameter of 87 um.

TxB: Intact microspheres, with an average diameter of 120 um.

TxC: Intact microspheres, with an average diameter of 144 um.

TxD: Intact microspheres, with an average diameter of 212 um.

TxE: Intact microspheres, with an average diameter of 244 um.

TxF: Intact microspheres, with an average diameter of 220 um.

TxG: Intact microspheres, with an average diameter of 116 um.

RG504H/RG502H Blends

TxA1: Intact microspheres, with an average diameter of 63 um.

TxB1: Intact microspheres, with an average diameter of 83 um.

TxC1: Intact microspheres, with an average diameter of 108 um.

TxD1: Intact microspheres, with an average diameter of 112 um.

TxE1: Intact microspheres, with an average diameter of 276 um.

TxF1: Intact microspheres, with an average diameter of 268 um.

TxG1: Intact microspheres, with an average diameter of 140 um.

4. Conclusions a. Paclitaxel loading efficiency was high using the copolymer blend methodology.

b. The structural stability of RG502(non-H and H)-containing paclitaxel microspheres was optimal with the copolymer blend methodology.

c. As the concentration of RG504, high molecular weight copolymer, increased, the size of the microsphere increased. This relationship held true for H series and non-H series copolymers.

d. As the concentration of RG502(non-H and H)increased, the paclitaxel release rate increased.

e. In comparing paclitaxel release rates at the end of the release period, paclitaxel formulations containing the H-series copolymers released paclitaxel at a rate 3–10 times greater than those containing the non-H series copolymers; therefore, the H-series copolymers significantly increased paclitaxel release rates.

f. The size of the microsphere was affected by the molecular weight of the copolymer, with predominantly H-series containing paclitaxel formulations having the smallest microspheres.

g. Smaller microspheres which contained a higher percentage of RG502(non-H and H) exhibited paclitaxel release rates faster than larger microspheres which contained a higher percentage of RG504(non-H and H).

C. Manipulation of System Parameters at the Microsphere Production Level to Further Increase Paclitaxel Release Rates 1. Purpose: The primary goal of this set of formulations was to further increase paclitaxel release rates by further manipulating system parameters at the microsphere production level.

2. System Parameters:

a. Sonication Stew: The paclitaxel/PLGA solution was sonicated with an aliquot of the external phase solution to form an emulsion. This emulsion resulted in the formation of small droplets of taxol and PLGA; therefore, smaller microspheres, on the order of 2–10 um in diameter, were produced.

b. Cooling Step: During the first half hour of stirring the paclitaxel PLGA in the external phase, the temperature of the external phase was maintained at 15 Celsius. This cooling facilitated the formation of smaller microspheres by minimizing the early aggregation of the small and numerous droplets of paclitaxel/PLGA.

c. External Phase Stir Rates: range of 250–1800 d. Formulation Specifics: 10% paclitaxel core loads (20 mg paclitaxel) with PLGA copolymer blend consisting of 90% RG502 (non-H and H) (162 mg) and 10% RG504 (non-H and H) (18 mg).

3. Results b. SEM Results

Tx54: Intact microspheres, with an average diameter of 2.5 um.

Tx55: Intact microspheres, with an average diameter of 2.0 um.

Tx56: Intact microspheres, with an average diameter of 9.6 um.

Tx57: Intact microspheres, with an average diameter of 3.0 um.

Tx58: Intact microspheres, with an average diameter of 7.0 um.

Tx59: Intact microspheres, with an average diameter of 11.0 um.

Tx60: Intact microspheres, with an average diameter of 40.0 um.

Tx61: Intact microspheres, with an average diameter of 49 um.

Tx62: Intact microspheres, with an average diameter of 32 um.

Tx63: Intact microspheres, with an average diameter of 12 um.

Tx64: Intact microspheres, with an average diameter of 18 um.

Tx65: Intact microspheres, with an average diameter of 17 um.

Tx66: Intact microspheres, with an average diameter of 26 um.

Advanced Development of Selected Paclitaxel/PLGA Formulations: Tx57. Tx9 and TxMedi a. preparation of Tx57

1) Set water bath to 15 C.
2) Prepare 1% poly-vinyl alcohol (PVA) in distilled water—500 ml
3) Co-dissolve paclitaxel powder and PLGA in 3.5 g methylene chloride (CH2C12)
4) Add this solution to 25 ml of 1% PVA in CH2C12-saturated distilled water
5) Homogenize five seconds (approx. 10,000 rpm)
6) Vortex 5 seconds
7) Add homogenized solution to the 500 ml PVA/water
8) Spin at 15 C. for ½ hour—stir rate 500 rpm
9) Spin at 15 C. for 4 hours—stir rate 500 rpm
10) Filter/wash spheres/vacuum dry at room temp overnight.

TABLE 3

Paclitaxel Core Loads

| Formulation | Stir Rate | Number of Bursts | Paclitaxel (ug/ml) | % Core Load | % Theoretical CL | % loading efficency | PLGA Type |
|---|---|---|---|---|---|---|---|
| Tx54 | 1800 | 4 | 68.315 | 6.737 | 10 | 67.372 | Non-H |
| Tx55 | 1800 | 4 | 76.381 | 7.43 | 10 | 74.300 | H |
| Tx56 | 1000 | 3 | 50.225 | 4.829 | 10 | 48.293 | Non-H |
| Tx57 | 1000 | 3 | 45.268 | 4.356 | 10 | 43.526 | H |
| Tx58 | 500 | 3 | 51.874 | 5.178 | 10 | 51.770 | Non-H |
| Tx59 | 500 | 3 | 48.738 | 4.677 | 10 | 46.774 | H |
| Tx60 | 700 | 3 | 43.282 | 4.174 | 10 | 41.738 | Non-H |
| Tx61 | 700 | 3 | 52.980 | 5.596 | 10 | 55.960 | H |
| Tx62 | 250 | 3 | 97.377 | 11.248 | 10 | 112.480 | Non-H |
| Tx63 | 250 | 3 | 106.140 | 11.997 | 10 | 119.970 | H |
| Tx64 | 500 | 1 | 106.125 | 12.370 | 10 | 123.700 | H |
| Tx65 | 500 | 0-vortex | 109.854 | 12.204 | 10 | 122.040 | H |
| Tx66 | 500 | 3 | 103.761 | 11.811 | 10 | 118.110 | H |

Paclitaxel Loading Efficiency 420100% b. Preparation of Tx9 and TxMedi

1) Set water bath to 15 C.
2) Prepare 1% PVA in distilled water—500 ml.
3) Co-dissolve paclitaxel powder and PLGA in 8.1 gCH2C12
4) Add this solution to 25 ml of 1% PVA in CH2C12-saturated distilled water
5) Vortex 5 seconds until consistency is milky/frothy.
6) Add vortexed solution to 500 ml of stirring PVA/water.
7) Spin 15 C. for ½ hours—stir rate 500 rpm
8) Spin 15 C. for 4 hours—stir rate 500 rpm
9) Filter/wash spheres/vacuum dry at room temp overnight C. Characterization of Tx57, Tx9, and TxMedi
6. Advanced Development of Selected Paclitaxel/PLGA Formulations: Tx20%. Tx40%. and Tx50%
   a. preparation of Microspheres
   1) Set water bath to 15 C. (run for ½ hour at this temp before starting).
   2) Prepare 1% PVA in distilled water—500 ml
   3) Co-dissolve paclitaxel powder and PLGA in 3.5 g CH2C12
   4) Add this solution to 25 ml of 1% PVA/CH2C12 saturated distilled water
   5) Homogenize (10,000 rpm/30 seconds in 50 ml centrifuge tube)
   6) Add homogenized solution to the 500 ml PVA/water
   7) Stir ½ hour at 15 C.—stir rate=650 rpm
   8) Stir 4 hours at 25 C.—stir rate=650 rpm
   9) Filter/wash spheres/vacuum dry overnight
   b. Characterization of Tx20%. Tx40%. and Tx50%
   In FIGS. 2,3,6, and 8 the amount of taxol released based on residual core load(res) data is more accurate than the amount released based on supernatant (sup) data.
   d. Conclusions
   1. The additional production level steps lowered paclitaxel loading efficiency because, most likely, these steps required the transfer of the paclitaxel/PLGA solution to multiple beakers.
   2. Addition of the previously mentioned steps resulted in significantly smaller microspheres, as compared to other batches of microspheres produced via methodology described in phase II, section A and B.
   3. Sonication and cooling steps resulted in the production of microspheres on the order of 2–10 um in diameter. Average microsphere diameter of microsphere populations was inversely proportional to the external phase stir rate; however, microsphere diameter ranges were highly variable. This variation was not as pronounced in microsphere populations produced via methodology described in phase II, section A and B.
   4. Intra-formulation range of microsphere diameters was great; therefore, overall patterns of paclitaxel release in response to the specific system parameters were slightly masked. Despite this technically, the general pattern of paclitaxel release was that H-series formulations released paclitaxel faster than non-H series formulations.
   5. Overall, the system parameters which accelerate paclitaxel release from PLGA are (a) the use of low molecular weight PLGA are: (a) the use of low molecular weight PLGA copolymer; (b) the use of high external phase stir rates; and (c) the sonication of the taxol/PLGA solution before external phase stirring.
D. Addition Of Sucrose into the Copolymer Matrix to Accelerate
Paclitaxel Release
   1. Purpose and Rationale: Incorporate an additive into the copolymer matrix to accelerate paclitaxel release. The rationale of this approach is that sucrose will immediately hydrolyze and create channels with the microsphere to allow for quicker hydration; thus, paclitaxel release should be significantly accelerated.
   2. System Parameters:
   a. Procedure: solvent extraction
   b. Stir Rate: 700 rpm for each batch
   c. Homogenization: 50% power, 30 second burst
   d. Polymer used RG501H
   e. Additive Used: sucrose (1.266%) or no sucrose
   f. Theoretical Paclitaxel Core Load: 10.127%
   3. Results
   a. Paclitaxel Cor e J,oads
   Batch 1 sucrose 10.724%
   Batch 2 (no sucrose) 10.398%
   b. SEM Results:
   Batch 1: Intact microspheres, with an average diameter of 6 um.
   Batch 2: Intact microspheres, with an average diameter of 5 um.
   C. In Vitro Paclitaxel Release (FIG. 8)
   d. Conclusions
   1. Sucrose within the matrix of the PLGA matrix accelerates paclitaxel release in comparison to release in the absence of sucrose.
   2. Paclitaxel release in the presence of sucrose was similar to other paclitaxel/PLGA formulations described above (compare FIG. 8 to FIG. 6). A potential reason for this may be that the percent sucrose within the PLGA matrix, which was 1.27% was not high enough to cause a significant increase in paclitaxel release.
   3. Additional paclitaxel/PLGA formulations containing more than 1% sucrose within the copolymer matrix are in the process of being prepared.
B. The Advantage of the Invention Over Presently Known Devices Systems, or Process.

Encapsulation of hydrophobic drugs in PLGA copolymer offers numerous advantages over standard hydrophobic drug administration. The advantages of biodegradable PLGA copolymer as a carrier for hydrophobic drugs include: (1) complete biodegradation, requiring no follow-up surgery to remove the drug carrier when the drug supply is exhausted (2,7); (2) biocompatibility(8); (3) ease of administration, in that anticancer drugs incorporated into biodegradable polymers can be administered via subcutaneous(s.c.) or intramuscular(i.m.) injection (2,9,10); and (4) the convenience of the biodegradable copolymer system itself, in terms of versatility and cost (2,7,9,11).

Most importantly, hydrophobic drugs incorporated into PLGA copolymer would allow for controlled release of the drug, as evidenced by drug release from previously reported lactide/glycolide drug delivery systems (2,7,10,12,13,14,15, 16).

A variety of chemotherapy (CT) drug delivery systems have been reported in the current literature; however, problems of poor, limited drug release from the drug carrier and of burst phenomenon are apparent. CT drugs are highly hydrophobic in nature; thus, CT drugs belong to the class of drugs which are illustrative of this invention.

Taxol encapsulated into liposomes prepared from phosphatidylglycerol and phosphatidylcholine were tested in mice bearing colon-26, a taxol resistant murine adenocarcinoma (17,18). Taxol encapsulated into poly-(e-caprolactone)(19) and into microspheres of ethylene vinyl acetate copolymer and poly(d,1-lactic acid) (20) have been tested for their ability to inhibit angiogenesis. Taxol encapsulated into nanocapsules composed of a polymeric wall of poly lactic acid have been tested in murine leukemia models; however, toxicity of the carrier was demonstrated (21). Overall, these studies show tumor growth inhibition and angiogenesis inhibition; however, the release kinetics of taxol in these systems, which range form 10–25% of the drug released in approximately 50 days, may be suboptimal, in terms of taxol dosages to be used clinically.

Cisplatin encapsulated in PLGA has been developed for local, intraperitoneal (i.p.) administration in the context of ovarian cancer (22) In vivo data indicated that i.p. administration of cisplatin/PLGA, as opposed to i.p. administration of an aqueous solution of cisplatin, increased the mean survival time of tumor-bearing rats; however, this formulation was not a stable cisplatin-releasing dosage form because of the burst phenomenon.

The conditions under which we encapsulate hydrophobic drugs (see section A) are specifically designed to overcome the limitations of the CT drug delivery systems described above.

C. Discussion of Problems Which the Invention is Designed to Solve.

The pharmacokinetics of systemically administered drugs is, typically, problematic in terms of efficacy and of toxicity. Standard i.v. administration of hydrophobic drugs, such as paclitaxel, results in alternating periods of overdose and drug inefficacy, while administration of controlled release drug formulations eliminates those peaks and valleys and provides a more constant systemic drug concentration over time (FIG. 9) (23) Systemic i.v. administration of taxol is the primary means of delivering potent CT drugs to cancer patients. Systemic CT is highly effective in cancer treatment, in terms of additional years of life gained as a result of therapy; however, there are many problems associated with systemic CT. CT drugs are highly cytotoxic (24), and, typically, large doses of CT drugs are needed to produce an optimal therapeutic response (24,25); therefore, CT drugs have a low therapeutic index (24).

Side effects commonly seen with standard CT dosages include: nausea, vomiting, fever, weight changes, hot flashes, musculoskeletal pain, alopecia, dermatitis, conjunctivitis, general malaise, and immune dysfunction (26,27). An additional side effect seen in patients treated with taxol is a severe hypersensitivity reaction due to Cremophor EL, taxol's solubilizing agent (17). Often, patients become so ill from CT that they have to be removed from treatment regimens (28). The consequence of this removal from therapy is fluctuating CT drug levels, which equate to decreased efficacy of CT drugs.

Figure 9:
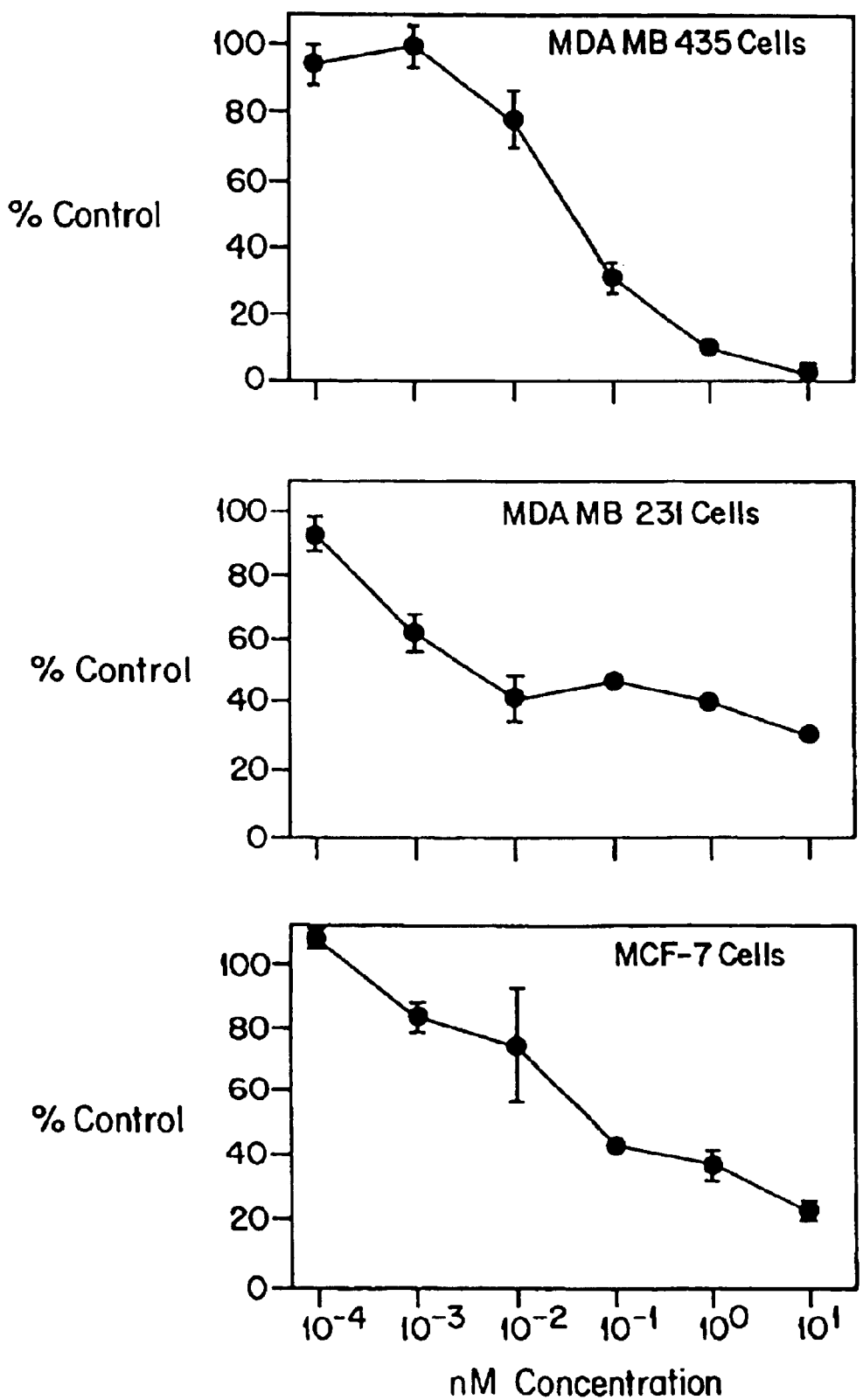
FIG. 9 shows the in vitro sensitivity of breast cancer cell lines to free taxol.

The PLGA copolymer technology discussed in this disclosure is designed to bypass the problematic pharmacokinetics of systemically administered drugs and the systemic toxicity typically associated with this mode of administration. The in vivo pharmacokinetics of a PLGA/drug formulation, in which there is controlled release of the drug from the PLGA copolymer, will, most likely, eliminate systemic toxicity (FIG. 9). At time 0 of standard i.v. drug therapy, a toxic amount of drug is delivered systemically. This toxic dose is a shock to the patient's biologic system, causing significant toxic side effects within a short period of time. This toxic drug level then rapidly drops to one of minimal effectiveness. This pattern ultimately results in a short exposure time of the biologic system to a therapeutic level of drug.

Drug release from a controlled release system is smooth and constant, with an extended period of time that the systemic concentration of the drug is at a therapeutic level. This extension is highly advantageous because it provides a more effective drug regimen. An additional medical concern when administering CT drug is that of drug interaction problems. Standard taxol CT requires pre-medication with corticosteroids, antihistamines, and histamine H2 receptor antagonists because of the toxicity of Cremophor EL. This pre-medication increases the potential for drug interactions that can affect taxol's pharmacokinetics and pharmacodynamics. As a PLGA copolymer formulation of this drug requires PLGA copolymer powder and taxol powder only, Cremophor EL can be eliminated from taxol CT; thus, taxol tolerability should be enhanced.

Given that hydrophobic drugs, such as CT drugs, are highly problematic under standard conditions of systemic administration, PLGA formulations for this class of drugs which minimize or eliminate systemic toxicity via controlled drug release will lead to more effective drug regimens and to a more efficient and economical use of this class of drugs.

D. List all Known and Other Possible Uses for the Invention

PLGA copolymer technology will provide clinicians with an alternative to systemic administration of hydrophobic drugs, such as taxol doxorubicin, 5-fluorouracil camptothecis, cisplatin, and metronidazole, which are problematic in terms of systemic toxicity complications. This alternative is that of a a.s.c./i.m. depot which control releases hydrophobic drugs. The advantages of this depot system in terms of hydrophobic drug delivery are: (1) improved patient compliance, as the number of drug dosings are decreased because the depot contains an amount of drug equivalent to multiple doses; (2) isolation depot from the tissue via its incorporation in PLGA thus reducing the drug concentration exposed to the one time and decreasing the chance of tissue injury of the drug copolymer, tissue at any at the depot site; (3) controlled drug release, which may allow for increased dosages of hydrophobic drugs to be administered without systemic toxicity complications. In terms of specific clinical applications of this technology, hydrophobic drug/PLGA formulations are envisioned to play a role in the treatment regiment of cancer and of infection.

Administration of paclitaxel/PLGA microspheres will offer a safer and a more effective means of delivering taxol to breast cancer patients than standard i.v. administration. Systemic taxol CT is now approved by the Federal Drug Administration (FDA) for the treatment of breast cancer after failure of combination CT for metastatic disease or after relapse within 6 months of adjuvant CT. The proposed paclitaxel/PLGA formulation will potentially, be used under the specific conditions as an alternative to systemic taxol CT. Additionally, the increased tolerability and efficacy of paclitaxel encapsulated in PLGA copolymer will, potentially, make this formulation an exemplary first-line CT agent for the treatment of breast cancer.

An expanded use of the proposed paclitaxel/PLGA formulation is envisioned Paclitaxel/PLGA may potentially be therapeutic for cancers other than breast cancer which are currently being treated with taxol CT regiments. Due to the increased tolerability of paclitaxel/PLGA, paclitaxel may be considered as a component of first-line CT regiments for tumors or various origin.

Additionally, the process of microencapsulating paclitaxel in PLGA copolymer is, most likely, capable of being applied to the microencapsulation of hydrophobic drugs other than paclitaxel. The microencapsulation technology used to prepare paclitaxel/PLGA microspheres is not specific to paclitaxel only, as it is a general chemical process. The advantages of microencapsulating paclitaxel in PLGA copolymers, in terms of improved tolerability and efficacy, are ones that can, most likely, be applied to any CT drug whose standard treatment results in undesirable systemic toxicity. Potential CT drugs to benefit from the PLGA copolymer technology described in this disclosure include: metronidazole, cisplatin, doxorubicin, camptothecin, and 5fluorouracil.

Moreover, this invention relates to and contemplates the use of the novel PLGA copolymer technology as a delivery system for bioactive agents such as heart drugs, like Capoten, Prinivil/Prinzidel; Vasotec, Pepcid,Mevacor, Antidepressents, like Prozac; arthritic drugs, like Naprosyn; antihistimines, like Claritin, Deconamine; anti-ulcer drugs, like Prilosec, Zantac; antiherpes drugs like Zovirax; Aids treatment drugs like, Crixivan, AZT; drugs for treating osteoporisis, like Esamax; blood pressure drugs; and drugs for the treatment of anxiety, diabetes, insomnia, alzheimer disease, migraine headaches, vitamins and diet regulating drugs, the active ingredient in each, derivatives and combinations thereof, or in combination with other bioactive agents.

E. List the Features of the Invention that are Believed to be Novel

Novel Features of Described Hydrophobic Drug/PLGA Formulations:

1. Hydrophobic drug/PLGA administration via the s.c. or i.m. route, a formulation which has the characteristics of: (1) depot formulation; (2) controlled drug release.

2. Elimination or significant decrease in the systemic toxicity of hydrophobic drugs, such as paclitaxel, cisplatin, doxorubicin, 5-fluorouracil, camptothecin, and metronidazole, due to the pharmacokinetics of controlled release drug formulations.

A) Produced sufficient quantities of our previously developed taxol/PLGA formulations for in vitro and in vivo testing.

B) Conduct in vitro analysis of the efficacy of taxol/PLGA using a taxol sensitive uterine sarcoma cell line and various human breast cancer cell lines.

C) Using a nude mouse xenograft model:

1) Establish a maximum tolerated dose for the series of taxol/PLGA formulations.

2) Compare the in vivo tumoricidal effect of taxol/PLGA to that of conventional administration of free taxol.

Methods Practiced

A) Production of taxol/PLGA Microspheres

1) Taxol/PLGA microspheres were prepared via solvent evaporation.

2) Core load, the percentage of taxol captured in the PLGA copolymer, was determined via HPLC using a pentylfluoryl phenyl column.

3) Morphology of taxol/PLGA microspheres were examined via SEM. Particle size distribution of the taxol/PLGA microspheres were calculated using the Accusizer Model 770 Single Particle Optical Sizer.

4) Taxol release from the PLGA copolymer were determined via taxol extraction using a SPE column and subsequent HPLC analysis.

B) In Vitro Analysis of the Efficacy of Taxol/PLGA Microspheres

1) Commercial cell lines used to test microspheres: ATCC CRL-1902; primary breast carcinoma, human; ATCC CRL-1897; breast carcinoma, human; ATCC CRL-1976; taxol sensitive uterine sarcoma, human. Institutional cell lines to be used to test microspheres: MDA MB 435 cells, MDA MB 231 cells, and MCF-7 cells, all of which are breast cancer cell lines.

2) Cell lines were subcultured to expand the line for subsequent in vitro testing.

3) Cells from each cell line will be tested in exponential growth phase. 24 hours post plating, wells will be treated with media only, media+free taxol (solubilized in Cremophor EL), or media+taxol/PLGA microspheres. Cells will be harvested 0,24,48, and 72 hours post taxol treatment for subsequent in vitro analysis. Taxol treatment of breast cancer cell lines is appropriate methodology to study the in vitro effect of taxol, as taxol/Cremophor EL treatment of various breast cancer cell lines has been shown to have anti-tumor effect, in terms of cytotoxicity (FIG. 9).

4) In vitro assays performed at each time point:

a) Proliferation of breast cancer cells: indices of proliferation of taxol treated breast cancer cell lines were determined using the MTT Assay Cell Titer Kit, a commercially available cell proliferation kit (Prometa, Madison, Wis.).

b) Cytocentrifuge slides of cells were stained using the Papanicolau staining procedure and will be examined for chromatin condensation and/or fragmented nuclei. Image analysis, examining parameters such as cell area, nuclear area, and cytoplasmic area, were performed using the Zeiss KT-400 image analysis system as the means of quantitating histologic data. As a separate staining procedure, cells will be stained with anti-cx-tubulin (Sigma, St. Louis, Mo.), a stain which binds the microtubule protein, tubulin. Staining was visualized using an AEC staining kit. Microtubular changes was examined via image analysis as the means of quantitating immunohistologic data.

C) In Vivo Analysis of the Efficacy of Taxol/PLGA Microspheres

Figure 10:
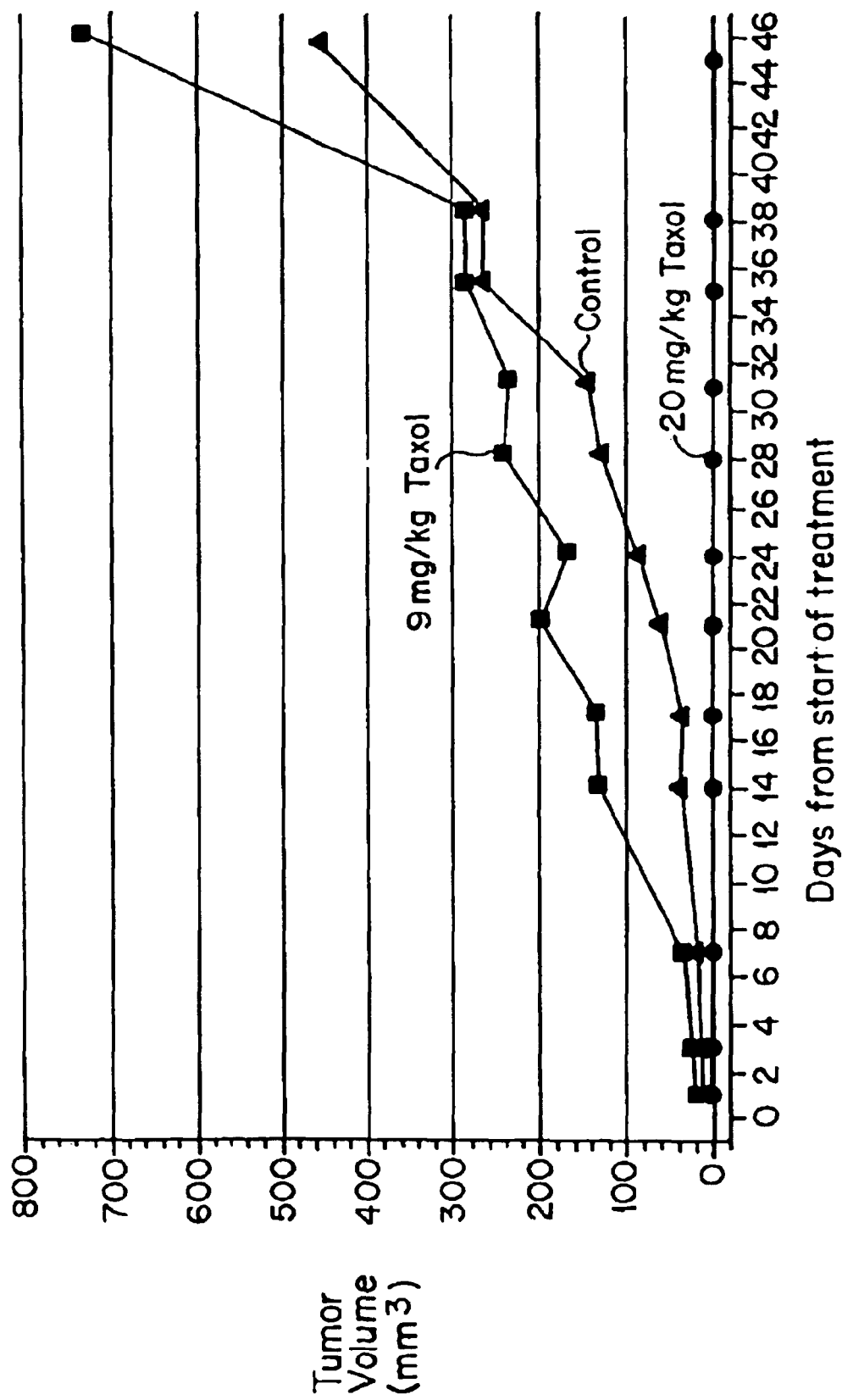
FIG. 10 shows the in vitro testing of free taxol on MDA MB 231 breast cancer xenografts in athymic mice.

1) The efficacy of taxol/PLGA microspheres was evaluated using a nude mouse xenograft model. This model has successfully and safely been used at the Lomardi Cancer Research Center, as evidenced by taxol/Cremophor El treatment of athymic nude mice carrying MDA 231 human breast cancer xenografts (FIG. 10). Briefly, mice will be inoculated s.c. into the mammary fat pads at 2 sites per mouse with 1×10 to 2×10 MDA 231 human breast cancer cells which have been MAP tested. Taxol treatment was begun 1–30 days post cell inoculation. Saline was the injection vehicle for the microspheres, and Cremophor EL was the injection vehicle for the free taxol. The taxol/Cremophor EL treatment schedule was approximately 3 weeks duration on a 5 day basis. The taxol/PLGA treatment schedule consisted of a one dose, i.m. or s.c. injection for the approximate 3 week duration.

2) Animals were sacrificed at specified time points during the treatment regimen.

3) Testing at animal-harvest time points:

a) Determination of the concentration of taxol in the serum and at the tumor site of taxol/PLGA treated animals via liquid-liquid extraction using diethyl ether and analysis of the dried organic phase via HPLC. Additionally, the HPLC methodology incorporates the use of an internal standard, N-nitrosodiphenylamine. Comparison of taxol concentration in response to taxol microsphere treatment to that in response to free taxol was made.

b) Evaluation of local toxicity of taxol/PLGA microspheres via examination of the injection sites and biopsy of the sites when necessary.

c) Evaluation of systemic toxicity of taxol/PLGA microspheres via a complete blood cell count and recorded weight changes was done. Comparison between taxol microsphere treated and free taxol treated animals was made.

Spore Animal Experiment #20:

Objective: Conduct toxicity study on microencapsualted taxol. Study will be done using C57/black, 6–8 week old, intact female mice. Animals will be injected (inocula volume=50 ul) on Day 0 either subcutaneously or intramuscularly. Each day they will be examined for signs of toxicity.

On days 2,4,6 & 8 animals will be weighted and one from each group will be sacrificed. A WBC will be done and serum collected. If any signs of toxicity are seen at the sight of injection, the site will be excised, fixed in 10% formalin, paraffin embedded and H&E's made.

Procedure:

Day 1—Randomize mice into 12 groups of 4 and ear notched & weigh

Day 9—Resolubilize microencapsulated taxol and control polymer—Weight animals and inject. RIGHT side will receive polymer control and LEFT side will receive encapsulated taxol Day 11—all animals Take on animal from each group, collect blood samples for WBC and serum. Check injection site for signs of toxicity. If signs exist, collect specimens.

Day 13—Day 11 procedure

Day 15—procedure

Day 17—procedure

*Everyday animals will be examined once in the morning and once in the evening for any signs of toxicity. If we see or deem morbidity inevitable, blood and specimens will be collected.

Treatment Groups:

| *Group # | Dose | Route |
|---|---|---|
| 1 | 0.04 mg/kg | Subcut |
| 2 | 0.4 mg/kg | subcut |
| 3 | 2 mg/kg | subcut |
| 4 | 4 mg/kg | subcut |
| 5 | 8 mg/kg | subcut |
| 6 | 16 mg/kg | subcut |
| 7 | 0.04 mg/kg | IM |
| 8 | 0.4 mg/kg | IM |
| 9 | 2 mg/kg | IM |
| 10 | 4 mg/kg | IM |
| 11 | 8 mg/kg | IM |
| 12 | 16 mg/kg | IM |

*Group # corresponds to Cage # on spread sheet, (Table 4)

Notes:

Injection site—no signs of animal at any time. This is true control, taxol, subq or IM, Weight—no signs of weight loss, on average the animals gained weight, WBC—no appreciable change in white blood cell count detected, Conclusion:

Since no signs of toxicity were determined, repeat study with high doses.

TABLE 4

SPORE #20: MICROENCAPSULATION TAXOL PK STUDY

| | Treatment Day | | Day 2 | Day 4 | | Day 6 | | Day 8 | |
|---|---|---|---|---|---|---|---|---|---|
| | 20 May 1997 | 23 May 1997 | 28 May 1997 | 01 Jun. 1997 | | 25 Jun. 1997 | | 5 Jul. 1997 | |
| Animal # | Weight (gm) | Weight (gm) | Weight (gm) | WBC | WBC | Weight (gm) | WBC | Weight (gm) | WBC |
| Cage 1 0.04 mg/kg subcut | | | | | | | | | |
| 1 | 16.15 | 18.00 | 18.65 | 5.9 | | | | | |
| 2 | 17.97 | 18.10 | 19.68 | | 19.77 4.1 | | | | |
| 3 | 18.16 | 19.20 | 17.40 | | 17.43 | 17.30 | 4.5 | | |
| 4 | 18.19 | 16.19 | 20.00 | | 20.18 | 20.50 | | 20.80 | 5.0 |
| Cage 2 0.4 mg/kg subcut | | | | | | | | | |
| 1 | 16.00 | 18.00 | 20.21 | 7.8 | | | | | |
| 2 | 16.97 | 18.82 | 20.23 | | 20.37 *3 | | | | |
| 3 | 18.04 | 18.25 | 19.21 | | 19.49 | 19.78 | 8.3 | | |
| 4 | 17.80 | 17.67 | 18.07 | | 18.91 | 19.15 | | 19.26 | 8.0 |
| Cage 3 2.0 mg/kg subcut | | | | | | | | | |
| 1 | 17.44 | 18.04 | 18.05 | 4.9 | | | | | |
| 2 | 18.00 | 18.04 | 18.01 | | 18.20 6.1 | | | | |
| 3 | 14.80 | 15.26 | 16.25 | | 18.38 | 16.93 | 4.3 | | |
| 4 | 17.71 | 17.90 | 20.00 | | 20.70 | 20.83 | | 20.96 | 8.6 |
| Cage 4 4 mg/kg subcut | | | | | | | | | |
| 1 | 17.60 | 18.10 | 19.87 | *3.1 | | | | | |
| 2 | 19.47 | 20.13 | 21.23 | | 21.92 2.5 | | | | |
| 3 | 15.78 | 15.80 | 21.11 | | 21.50 | 21.70 | 6.1 | | |
| 4 | 16.92 | 16.90 | 18.31 | | 18.51 | 19.30 | | 19.23 | 6.5 |
| Cage 5 8 mg/kg subcut | | | | | | | | | |
| 1 | 17.09 | 17.12 | 19.02 | 5.9 | | | | | |
| 2 | 19.70 | 19.92 | 18.14 | | 19.22 7.2 | | | | |
| 3 | 17.00 | 17.10 | 19.04 | | 19.30 | 19.22 | 4.5 | | |
| 4 | 16.98 | 17.00 | 17.82 | | 19.40 | 18.32 | | 18.54 | *3.8 |
| Cage 6 16 mg/kg subcut | | | | | | | | | |

TABLE 4-continued

SPORE #20: MICROENCAPSULATION TAXOL PK STUDY

| | Treatment Day | | Day 2 | Day 4 | | Day 6 | | Day 8 | |
|---|---|---|---|---|---|---|---|---|---|
| | 20 May 1997 | 23 May 1997 | 28 May 1997 | 01 Jun. 1997 | | 25 Jun. 1997 | | 5 Jul. 1997 | |
| Animal # | Weight (gm) | Weight (gm) | Weight (gm) | WBC | WBC | Weight (gm) | WBC | Weight (gm) | WBC |
| 1 | 17.54 | 17.62 | 18.32 | | 17.91 | 6.1 | | | |
| 2 | 18.11 | 18.00 | 19.40 | | 21.30 | 20.39 | 5.3 | | |
| 3 | 16.80 | 16.80 | 21.09 | | 17.01 | 21.08 | | 20.81 | *3.5 |
| 4 | 15.98 | 15.90 | 16.12 | 6.4 | | | | | |

Taxol Quantitation in Mouse Serum Samples Performed by USADRD-WRAIR

A. Development of HPLC Procedure: Analyzing Taxol Content in House Serum

1. Procedure
   a. Taxol stock (1.06 mg/ml) was prepared in 100% acetonitrile.
   b. A set of taxol standards were made in 100% acetonitrile (0.53 ug/ml–106 ug/ml) from the taxol stock for use to generate a taxol calibration curve.
   c. A set of taxol standards were made in mouse serum (Sigma) from the taxol stock (5.30 ug/ml–106 ug/ml).
   d. Taxol/serum standards were prepared for subsequent HPLC analysis via 2 procedures. Procedure 1 was extraction of taxol via acetonitrile precipitation of serum proteins, and procedure 2 was extraction of taxol via solid phase extraction (SPE).
   e. Acetonitrile Precipitation: Taxol/serum standards were diluted 1:2 or 1:10 using acetonitrile and centrifuged for 5 minutes at 6,000 rpm. The supernatant was collected for HPLC analysis. Sample volume for HPLC analysis was 700 ul.
   f. Solid Phase Extraction: 5 ml of a 90:10 distilled water/acetonitrile solution were added to SPE columns (lgC18;6cc; Extra sep column; Thomson Instrument Company) to wet the columns. 100 ul of taxol/serum standard (1:10 dilution) or 500 ul of taxol/serum standard (1:2 dilution) were added to the SPE column. Serum proteins were washed from the SPE column using 90:10 distilled water/acetonitrile, and taxol was eluted from the SPE. column using 1 ml of acetonitrile. 700 ul of taxol/acetonitrile were used for subsequent HPLC analysis.

2. HPLC Method
   a. Mobile 50—50 acetonitrile/distilled water with 0.1% phosphoric acid
      b. Column: PFP, 5 micron, 250×4.6 mm (Column Engineering, Inc.)
   c. Flow Rate: 1 ml/min; isocratic
   d. 4 Wavelength: 227 nm 2. Results: Percent Efficiency of Taxol Recovery from Taxol/Serum Standards
   a. Acetonitrile Precipitation: 1:2 dilution
      5.30 ug/ml=61.43%
      10.6 ug/ml=55.17%
      26.5 ug/ml=54.29%
      53.0 ug/ml=55.18%
      106 ug/ml=51.60%
   b. Acetonitrile Precipitation: 1:10 dilution
      5.30 ug/ml=121.89%
      10.6 ug/ml=108.21%
      26.5 ug/ml=104.98%
      53.0 ug/ml=101.87%
      106 ug/ml=99.27%
   c. Solid Phase Extraction: 1:2 dilution
      5.30 ug/ml=29.87%
      10.6 ug/ml=29.85%
      26.5 ug.ml=25.21%
      53.0 ug/ml=23.67%
      106 ug/ml=22.86%
   d. Solid Phase Extraction: 1:10 dilution
      5.30 ug.ml=128.49%
      10.6 ug.ml=115.85%
      26.5 ug/ml=63.36%
      53.0 ug/ml=59.06%
      106 ug/ml=3.34%
   e. This experiment was repeated with similar taxol recovery rates.

3. Conclusions
   a. Efficiency of taxol recovery from acetonitrile precipitation was higher than that from solid phase extraction, although a smaller SPE column may also be effective.
   b. Serum protein interference appeared to,be minimized using the acetonitrile precipitation (1:1O dilution) method.
   c. Method selected for subsequent use was: acetonitrile precipitation (1:10 dilution).

3. Validation of Internal Standard Incorporation into the
   1. Procedure
   a. A 1 mg/ml stock solution of N-nitrosodiphenylamine (NDA), the internal standard, was prepared in 100% acetonitrile.
   b. A 30 ug/ml NDA solution was prepared from the NDA stock solution in 100% acetonitrile.
   c. A set of taxol standards in mouse serum (Sigma) were prepared in 1.5 ml microfuge tubes containing NDA (100 ul of 30 ug/ml stock) and taxol. Taxol standard concentrations were as follows: 1.11 ug/ml, 2.22 ug/ml, 3.33 ug/ml, 5.55 ug/ml, and 11.1 ug/ml.
   d. Standards were spun for 1 min at 7,000 rpm, and 700 ul of the resulting supernatant were analyzed via HPLC.
   e. 2 calibration curves were prepared, one using NDA as the internal standard and the other using taxol alone. Calibration standards used.were: 1.0 ug/ml, 2.0 ug/ml, 5.0 ug/ml, and 10 ug/ml. The 3.0 ug/ml standard was run 10 times, and the amount was quantitated using each calibration curve.

2. HPLC Method
   a. Same method as used in Section A.
3. Results
   a. Calibration Curve Without NDA
      1) R2=0.98533 (all standard points included)
      2) Average concentration of the 10–3.33 ug/ml runs=2.946 (88.45% efficiency)
   b. Calibration Curve With NDA
      1) R2=0.999535 (all standard points included)
      2) Average concentration of the 10–3.33 ug/ml runs=3.246 (98.36% efficiency)
4. Conclusions
   a. Accuracy is significantly improved using the internal standard. This internal standard will be used to analyze the serum samples from the in vivo experiment.

Figure 21B:
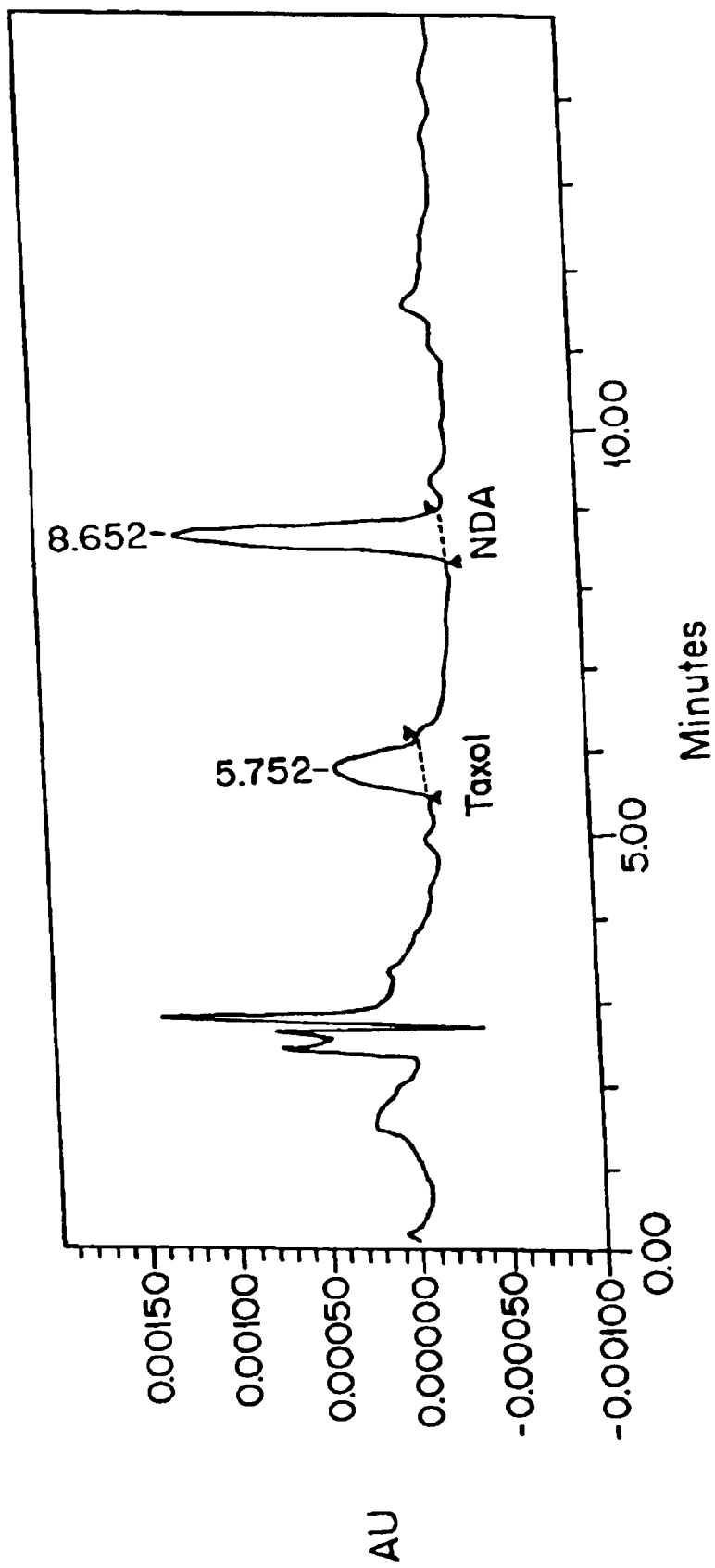
FIG. 21 shows HPLC chromatograms of (A) HPLC grade acetonitrile blank; and (B) 100 ng/ml taxol standard containing NDA, the internal standard.
Figure 22A:
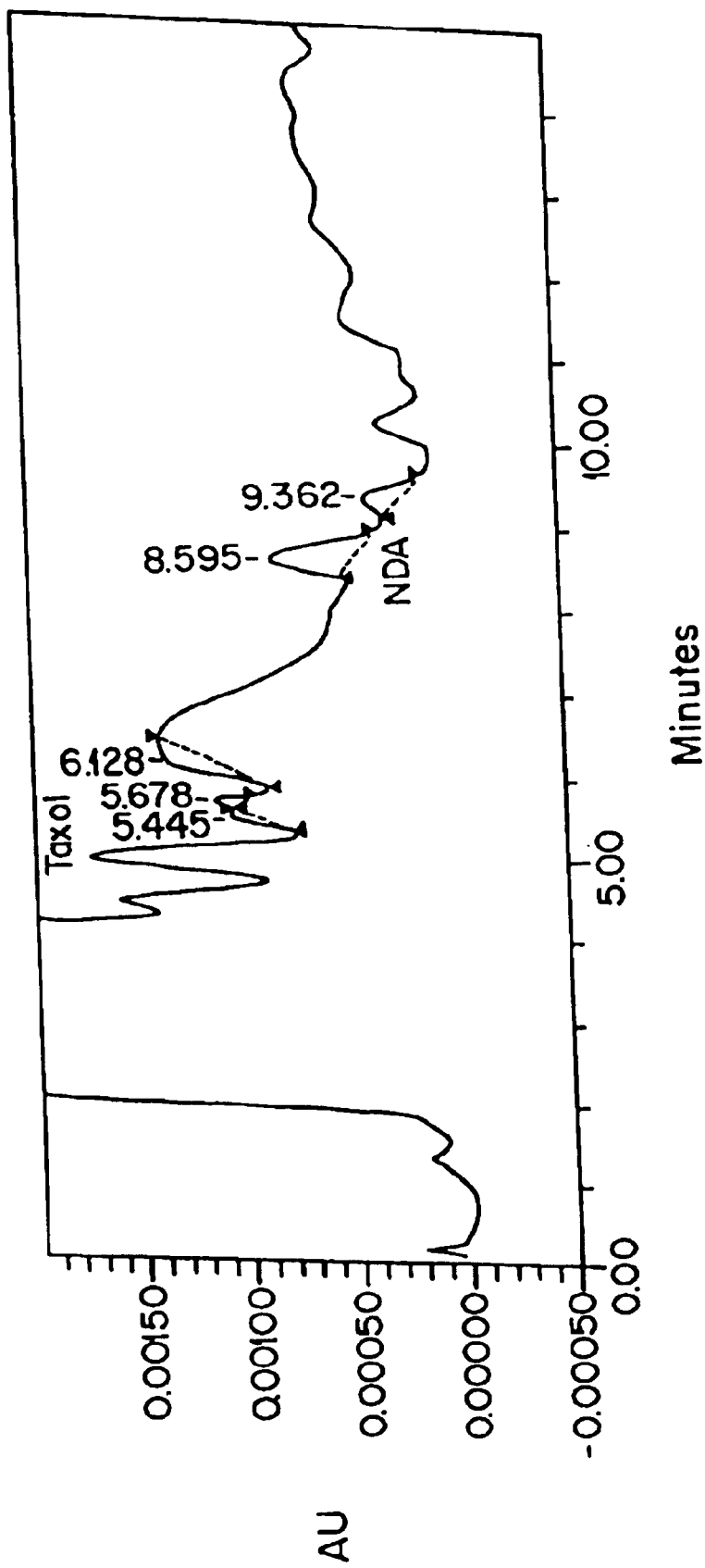
FIG. 22 shows the HPLC chromatograms of (A) G6#1 (16 mg/ml; s.c. route; group 1. and (B) G12#1 (16 mg/ml; i.m. route;group 1).
Figure 22B:
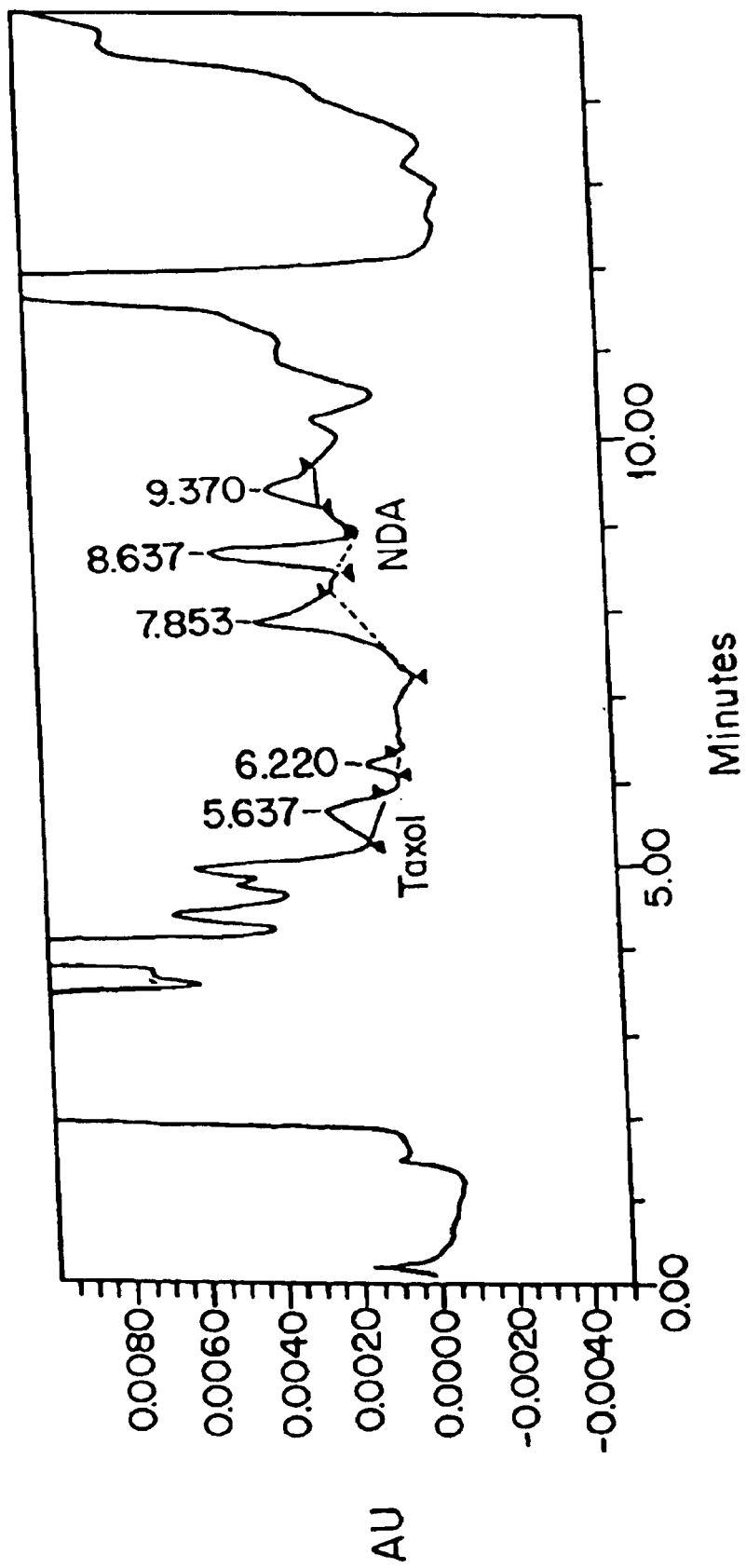

C. Taxol Quantitation in Mouse Serum Samples
1. Sample Preparation
   a. 100 ul of serum were transferred to a microfuge tube.
   b. 25 ul of NDA stock (2.12 ug/ml) were added to the serum.
   c. 876 ul of acetonitrile were added to the serum/NDA.
   d. The microfuge tube was vortexed for 30 seconds and then centrifuged for 30 seconds at 7,000 rpm.
   e. 600 ul of the resulting supernatant was transferred to an HPLC vial for analysis.
   f. Taxol standards were prepared in serum. Total volume was 1 ml. Taxol standard concentrations were: 28 ng/ml, 56 ng/ml, 84 ng/ml, and 112 ng/ml.
   note: Many of the serum samples were moderately—grossly hemolyzed.
2. BPLC Methods Applied
   a. Method 1
      (1) Mobile Phase: 50—50 acetonitrile/distilled water with 0.1% phosphoric acid
      (2) Column: PFP, 5 micron, 250×4.6 mm (Column Engineering, Inc.).
      (3) Flow Rate: 1 ml/min; isocratic
      (4) Wavelength: 227 nm
      (5) Results: In comparison with taxol standards, a peak which appeared to be composed of 2 elements was detected at the retention time of taxol; however, since the peak: noise ratio was so low, identification of the peak(s) as taxol was not possible. Additionally, due to interference from a component in the sample, quantatation of the peak(s) was not possible.
      (6) Additional Parameters Tested using this method:
   Increased acetonitrile concentration up to 75% in order to resolve the multi-element peak; however, no increase in peak resolution was observed.
   b. Method 2
      (1) Mobile Phase: 70:30 acetonitrile/distilled water with 0.1% phosphoric acid
      (2) Column: Inertsil; 5 um; ODS-2; 250×3 mm ID
      (3) Flow Rate: 0.4 ml.min isocratic
      (4) Wavelength: 227 nm
      (5) Results: This column was tried in order to increase peak resolution and to positively identify the peak(s) in question. We were not able to accomplish this task; however; we were able to produce a calibration curve using mouse serum (Sigma) in the nanogram range. R2 for this calibration curve was 0.991273. Again, concentrations of taxol were much too low for analytical analysis.
   (c) Method 3
      (1) Mobile Phase: 60:40 acetonitrile/distilled water with 0.1% phosphoric acid
      (2) Column: Inertsil; 5 um; ODS-2, 250×3 mm ID
      (3) Flow Rate: 0.4 ml/min
      (4) Wavelength: 227 nm
      (5) Results: We were able to separate the multi-element peak slightly; however, this separation was not yet optimal, and the band broadening affected the integration of the taxol peak at low nanogram levels. We were able to produce a calibration curve using mouse serum (Sigma) in the nanogram level; however, integration was impossible due to the band broadening effect. Again, concentration of taxol were much too low for analytical analysis.
   d. Method 4-Gradient Method
      (1) Mobile Phase: Solvent A=distilled water with 0.15 phosphoric acid; Solvent B=acetonitrile
      (2) Columns and Flow Rates: Intertsil ODS, 3 mm ID(0.4 ml/min); Reliasil ODS, 3 um, 100 A, 2.1 mm ID×150 (0.4 ml/min; Reliasil ODS 5 um, 300 A, 2.1 mm ID×150(0.2 ml/min)
      (3) Gradient: 40–80% solvent B in 20 min
      (4) Wavelength: 227 nm
      (5) Results: Separation was not effective.
   e. Method 5
      (1) Mobile Phase: 65:35 acetonitrile/distilled water with 0.1% phosphoric acid
      (2) Column: Inertsil; 5 um; 58.ODS-2; 25O×3 mm ID
      (3) Flow Rate: 0.4 ml/min; isocratic using a photodiode array detector
      (4) Wavelength: 227 nm
      (5) Results: Separation of the multi-element peak was accomplished; however, due to interference and the extremely low taxol concentrations, positive identification/quantitation was not possible. FIGS. 21 and 22 show representative chromatograms of our best effort to give an indication of the range that we had to work with. Taxol retention time was 5.572 minutes, and NDA retention time was 8.652 minutes (FIG. 21B). Working at the nanogram level makes background peaks more important, in terms of their contribution to the taxol peak height and area. Analyzing an HPLC grade acetonitrile blank showed interference which amounted to approximately 23% of the area of the taxol peak in the 100 ng/ml standard, while no interference with the NDA peak was observed (compare FIG. 21A to. FIG. 21B). FIG. 22 shows chromatograms of serum samples G6#1(16 mg/ml; s.c. route; group 1) and G12#1(16 mg/ml; i.m. route; group 1)—Taxol concentrations were just too low to reliably work with (FIG. 22).
3. Conclusions
   a. Trace amounts of taxol (in the low nanogram range) in the serum samples were detected; however, concentrations were just too low to reliably support this observation. A more concentrated sample/larger sample is required to increase the peak: noise ratio, thus, improving quantitation ability. Our next experiment using higher concentrations of taxol may allow us to verify that taxol is leaving the depot site and entering the systemic circulation. Additionally, peak interference was a problem. This interference could have been due to: (1) acetonitrile; (2) serum protein(s);(3) specimen hemolysis; (4) taxol metabolites. Methodologies to further "clean" up the sample need to be employed.

b. Taxol is metabolized quickly; therefore, detection of parent drug may be difficult due to interference with taxol metabolities. Amplification of the taxol signal may be accomplished using W chromophore derivatization specific for functional chemical groups within the parent drug. These UV chromophores may also amplify metabolite detection. Additionally, serum protein(s)/acetonitrile interference with out peak of interest in the nanogram range may be eliminated with amplification of the desired signal.

4. Additional Steps During Sample Preparation To Overcome Problems a. Using a smaller bed SPE column and/or liquid/liquid extraction using diethyl ether. These steps would allow for a smaller reconstitution volume, which may increase sensitivity.

b. Signal amplification using W chromophore derivatization.

BIBLIOGRAPHY

1. Young, J. L., Jr. 1989. Incidence and mortality of breast cancer in Breast Cancer, B. J. Kennedy, editor. Alan R. Liss, Inc., New York, N.Y. p.105.
2. Wood, W. C. 1989. Definitive surgery for stages I and II breast cancer in Breast Cancer, B. J. Kennedy, editor, Alan R. Liss, Inc., New York, N.Y. p.95.101.
3. Boyages, J. and J. R. Harris. 1989. Conservative surgery and radiation therapy for stages I and II breast cancer in Breast Cancer. B. J. Kennedy, editor. Alan R. Liss, Inc., New York, N.Y. p.102–111.
4. Rausch, D. J., T. Kiang, and B. J. Kennedy. 1989. Guidelines for management of breast cancer: a treatment summary in Breast Cancer, B. J. Kennedy, editor. Alan R. Liss, Inc., New York, N.Y. p.225–239.
5. Chu, F. F. C. 1987. Radiation therapy following local excision or partial mastectomy in Breast Cancer: Diagnosis and Treatment: I-M. Ariel R. Liss, Inc., New York, N.Y. p.43–161.
6. Abrams, J. S. and J. Aisner. 1989. The evolving approach to stage III breast cancer in Breast Cancer, B. J. Kennedy, editor. Alan R. Liss, Inc., New York, N.Y. p.43–161.
7. Booser, D. J. and G. N. Hortogagy. 1992. Treatment of locally advanced breast cancer. Semin. Oncol. 19(3): 278–285.
8. Fowble, B. and D. Glover. 1991. Locally advanced breast cancer in Breast Cancer Treatment: A Comprehensive Guide to Management. B. Fowble, R. L. Goodman, J. G. Glick, and E. F. Rosato, editors. Mosby Year Book, St. Louis, Mo. p.345–372.
9. Henderson, I. C. 1989. Adjuvant systemic therapy of breast cancer in Breast Cancer, B. J. Kennedy, editor. Alan R. Liss, Inc., New York, N.Y. p.113–141.
10. Taylor, S. G., IV. 1989. Advanced breast cancer management; chemotherapy in Breast Cancer, B. J. Kennedy, editor. Alan R. Liss, Inc., New York, N.Y. p.173–187.
11. Dordunoo, S. K., J. K. Jackson, L. A. Arsenault, A. M. C. Oktaba, W. L. Hunter, and H. M. Burt. 1995. Taxol encapsulation in poly(e=caprolactone)microspheres. Cancer Chemother. Pharmacol. 36:279–282.
12. Burt, H. M., J. K. Jackson, S. K. Bains, R. T. Liggins, A. M. C. Oktaba, A. L. Arsenault, and W. L. Hunter. 1995. Controlled delivery of taxol from microspheres composed of a blend of ethylene-vinyl acetate copolymer and poly (d,l-lactic acid). Cancer Lett. 88: 73–79.
13. Kunieda, K., T. Seki, S. Nakatani M. Wakabayashi, T. Shiro, K. Inoue, M. Sougawa, R. Kimura, and K. Harada. 1993. Implantation treatment method of slow release anticancer doxorubicin containing hydroxyapatite (DOX-HAP) cinokexL a basuc study of a new treatment for hepatic cancer. Br. J. Cancer 67:668–673.
14. Gasparini, A., M. Tonetti, B. Astroff, L. Rowe, W. Satterfield, R. Schmidt, and J. R. DeLoach. 1992. Pharmacokinetics of doxorubicin loaded and glutaraldehyde treated erythrocytes in healthy and lymphoma bearing dogs in The Use of Resealed Erythrocytes as Carriers and Bioreactors, M. Magnani and J. R. DeLoach, editors. Plenum Press, New York, N.Y. p.299–304.
15. Kies, M. S. 1987. Adjuvant chemotherapy of breast cancer in Breast Cancer: Diagnosis and Treatment. I. M. Ariel and J. B. Cleary, editors. McGraw-Hill Book Company, New York, N.Y. p.328–343.
16. Seidman, A. D., D. Hochhauser, M. Gollub, B. Edelman, T. Yao, C. A. Hudis, P. Francis, D. Fennely, T. A. Gilewski, M. E. Moynahan, V. Currie, J. Baselga, W. Tong, M. O'Donahue, R. Salvaggio, L. Auguste, D. Spriggs, and L. Norton. 1996. Ninety-six hour paclitaxel infusion after progression during short taxane exposure; a phase II pharmacokimetic and pharmacodynamic study in metastatic breast cancer. J. Clin Omcol 146:1877–1884.
17. Sharma, A., E. Mayhew, and R. M. Straubinger. 1995. Antimor effect of taxol-containing liposomes in a taxol-resistant murine numor model. Cancer Res. 53:5877–5881.
18. Straubinger, R. M., A. Sharma, M. Murray, and E. Mayhew. 1993. Novel taxol formulations: taxol-containing liposomes. Monogr, Natl. Cancer Inst. .15:69–78.
19. Bartoli, M. H., M. Boitard, H. Fessi, H. Beriel, J. P. Devissaguet, F. Picot. and F. Puisieux. 1990. In vitro and in vivo tumoricidal activity of free and encapsulated taxol. Microencapsulation 7(2):191–197.
20. Jampel, H. D., D. Thibault, K. W. Leong, P. Uppal, and H. A. Quigley. 1993. Glamcoma filtration surgery in nonhuman primates; using taxol and etoposide in polyamhydride carriers. Invest. Ophthalmol. Vis. Sci. 34:3076–3083.
21. Winternitz, C. I., J. K. Jackson, A. M. Oktaba, and H. M. Burt. 1996. Development of a polymeric surgical paste formulation for taxol. Pharm. Res. 13(3):368–375.
22. Innocenti, F., R. Danesi, A. dipaolo, C. Agen, D. Nardini. G. Bocci and M.del Tacca. 1995. Plasma and tissue disposition of paclitaxel(taxol) after intraperitoneal administration in mice. Drug Metabolism and Disposition 23(7): 713–717.
23. Lewis, D. H. 1990. Controlled release of bioactive agents from lactide/glycolide polymers in Biodegradable Polymers as Drug Delivery Systems. M. Chasin and R. Langer. editors. Marcel Dekker, Inc., New York, N.Y. p1–41.
24. Zhifang, Z., Z.Mingxing, W. Shengao, L. Fang, and S. Wenzhao. 1993. Preparation and evaluation in vitro and in vivo copoly(lactic/glycolic) acid microspheres containing norethisterone. Biomat. Art. Cells Immob. Biotech. 21(1): 71–84.
25. Visscher, G. E., R. L. Robinson, and G. J. Argentieri. 1987. Tissue response to biodegradable injectable microcapsules. J. Biomat. Applic. 2:118–131.
26. Toguchi, H. 1991. Formulation study of leuprorelin acetate to improve clinical performance. Clin. Therap. 14(Suppl A):1210 128.
27. Balant, L. P. 1993. Regulatory aspects of modified release dosage forms: clinical studies. Boll. Chim. Farmaceutico 1332(5):143–149.

28. Redding, T. W., A. V. Schally, T. R. Tice, and W. E. Meyers. 1984. Long-acting delivery systems for peptides: inhibition of rat prostate tumors by controlled release of (D-up) luteinizing hormone-releasing hormone from injectable microspheres. Proc. Natl. Acad. Sci. USA 81:5845–5848.
29. Moritera, T., Y. Ogura, N. Yoshimura, Y. Honda, R. Wada, S. H. Won, and Y. Ikada. 1992. Biodegradble microspheres containing adriamycin in the treatment of proliferative vitreoretinopathy. Invest. Ophthalmol. Vis. Sci 33:3125–3130.
30. Rosen, H. B., J. Kohn, K. Leong, and Langer. 1988. Bioerodible polymers for controlled release systems in Controlled Release Systems: Fabrication Technology. volume II. D. Hsieh, editor. CRC Press, Inc., Boca Raton, Fla. p.84–110.
31. Lewis, D. H. 1990. Controlled release of bioactive agents from lactide/glycolide polymers in Biodegradable Polymers as Drug Delivery Systems, M. Chasin and R. Langer, editors. Marcel Dekker, Inc., New York, N.Y. p.1–41.
32. Kingston, D. G. I. 1991. The chemistry of taxol. Pharmac. Ther. 52:1–34.
33. Rowinsky, E. K. L. A. Cazenave, and R. C. Donehower. 1990. Taxol: a novel investigational antimicrotubule agent. J. Natl. Cancer Inst. 82:1247–1259.
34. Schiff, P. B., J. Fant, and S. B. Horwitz. 1979. Promotion of microtubule assembly in vitro by taxol. Nature 277:665–667.
35. Kearns, C. M., L. Gianni, and M. J. Egorin. 1995. Paclitaxel pharmacokinetics and pharmacodynamics. Semin. Oncol. 22(3): 16–23.
36. Zhifang, Z., Z. Mingxing, W. Shengao, L. Fang, and S. Wenzhao. 1993. Preparation and evaluation of in vitro and in vivo copoly(lactic)acid microspheres containing norethisterone. Biomet. Art. Cells Immob. Biotech. 21(1): 71–84.
37. Visscher, G. E., R. L. Robinson, and G. J. Argentieri. 1987. Tissue response to biodegradable injectable microspheres. J.Biomat. Applic. 2:118–131.
38. Toguchi, H. 1992. Formulation study of leuprorelin acetate to improve clinical performance. Clin. Therap. 14(Suppl.A): 121–128.
39. Balant, L. P. 1993. Regulatory aspects of modified release dosage forms: clinical studies. Boll. Chim. Farmaceutico 132(5): 143–149.
40. Moritera, T., Y. Ogura, N. Yoshimura, Y. Honda, R. Wada, S. H. Won r and Y. Ikada. 1992. Biodegradable microspheres. containing adriamycin in the treatment of proliferative vitreoretinopathy. Invest. Ophthalmol. Vis.Sci 33:2125–2130.
41. Redding, T. W., A. V. Schally, T. R. Tice, and W. E. Meyers. 1984. Long-acting delivery systems for peptides: inhibition of rat prostate tumors by controlled release of (D-trp6) luteinizing hormone-releasing hormone from injectable microcapsules. proc. Natl. Acad. Sci. USA 81:5845–5848. 66.42. Jacob, E., J. A. Setterstrom, D. E. Black, Jr., J. R. Heath, III; and others. 1991. Evaluation of biodegradable ampicillin anhydrate microcapsules for local treatment of osteomyelitis in a rabbit model. Clin. Orthop. 267:237–244.
43. Jacob, E., G. Cierny, M. T. Fallon, J. F. McNeill, Jr., and G. S. Siderys. 1993. Evaluation of biodegradable cefazolin sodium microspheres for the prevention of infection in rabbits with experiemental open tibial fractures stabilized with internal fixation. J. Orthop. Res. 11(3):401–411.
44. Setterstrom, J. A., T. R. Tice, and W. E. Myers. 1984. Development of encapsulated antibiotics for topical administration to wounds in Recent Advances in Drug Delivery Systems. J. M. Anderson and S. W. Kim, editors, Plenum Publ. Corp., New York, N.Y. p.185–198.
45. Rethman, M. P., J. A. Setterstrom, E. Jacob, J. R. Health, and D. Polly. 1988. Locally applied microencapsualted ampicillin anhydrate obvious S. aureus infection of internally fixed fractures in rats. J. Dent. Res. (sp.Issue) 67:298.
46. Sharma, A., E. Mayhew, and R. M. Straubinger. 1993. Antitumor effect of taxol-containirrg.liposomes in a taxol-resistant tumor model. Cancer Res. 53:5877–5881.
47. Straubinger, R. M., A. Sharma, M. Murray, and E. Mayhew. 1993. Novel taxol formulations: tax0l containing liposomes. Monogr. Natl. Cancer Inst. 15:69–78.
48. Dordumoo, S. K., J. K. Jackson, L. A. ArSenaUlt, A. M. C. Oktaba, W. L. Hunter, and H. M. Burt. 1995. Taxol encapsulation in poly-(e-caprolactone) microspheres. Cancer Chemother. Pharmacol. 36:279–282.
49. Burt, H. M., J. K. Jackson, S. K. Bains, R. T. Liggins, A. M. C. Oktaba, A. L. Arsenault, and W. L. Hunter. 1995. Controlled delivery of taxol from microspheres composed of a blend of ethylene-vinyl acetate copolymer and poly (d,l-lactic acid). Cancer Lett. 88:73–79.
50. Bartoli, M. H., M. Boitard, H. Ressi, H. Beriel, P. Devissaguet, F. Picot, and F. Pusieux. 1990. In vitro and in vivo tumoricidal activity of free and encapsulated taxol. J. Microencapsulation 7(2): 191–197.
51. Kumagai, S., T. Sugiyama, T. Nishida, K. Ushijima, and M. Yakushiji. 1996. Improvement of intraperitoneal chemotherapy for rat ovarian cancer using cisplatin-containing microspheres. Jpn. J. Cancer Res. 87–412–417.
52. Sinko, P. and J. Kohn. 1993. Polymeric drug delivery systems—an overview ACS Symposium Series, 520:18–41.
53. Kunieda, K., T. Seki, S. Nakatani, M. Wakabayashi, T. Shiro, K. Inoue, M. Sougawa, R. Kimura, and K. Harada. 1993'. Implantation treatment and method of slow release doxorubicin containing hydroxyapatite (DOX-HAP) complex. A basic study of a new treatment for hepatic cancer. Br. J. Cancer 67:668–673.
54. Gasparini, A., M. Tonetti, B. Astroff, L. Rowe, W. Satterfield, R. Schmidt, and J. R. DeLoach. 1992. pharmacokinetics of doxorubicin loaded and glutaraldehyde treated erythrocytes in healthy and lymphoma bearing dogs in The Use of Resealed Erythrocytes as Carriers and Bioreactors. M. Magnani and J. R. DeLoach, editors.
55. Henderson, I. C. 1989. Adjuvant systemic therapy of breast cancer in Breast Cancer, B. J. Kennedy, editor. Alan R. Liss, Inc., New York, N.Y. p.113–141.
56. Kies, M. S. 1987. Adjuvant chemotherapy of breast cancer in Breast Cancer Diagnosis and Treatment, I. M. Ariel and J. B. Cleary, editors. McGraw-Hill Book Company, New York, N.Y. p.3280 343.
57. Shikan, A. H., D. W. Eisels, and A. J. Domb. 1994. Polymer delivery of chemotherapy for squamous cell carcinoma of the head and nect. Arch. Otolaryngol: Head Neck Surg. 120:1242–1247.

This invention relates to the design of biocompatible and biodegradable microspheres for novel, sustained release of hydrophobic agents alone, including paclitaxel, doxorubicin, 5-fluorouracil, camptothecin, cisplatin, metronidazole, and combinations, derivatives, or functionally equivalents thereof, or in combination with hydrophillic agents over a period of up to 100 days in an aqueous physiological environment with little or no burst release.

Unlike currently available release systems which rely on the use of filler/additives such as gelatin, albumin, dextran, pectin, polyvinyl pyrrolidone, polyethylene glycol, sugars, etc., and are still prone to low encapsulation efficiencies and "burst effects", this invention achieves high encapsulation efficiency and "burst-free", programmable sustained release is achieved. The excipients used in the formulation (PLGA) have molar compositions ranging from 100/O to 50/O lactide/glycolide with molecular weight of lo-100 kDa.

Additionally, two forms of the biocompatible, biodegradble poly(DL/lactide-shield-glycolide) can be employed, one being the more hydrophobic end-capped polymer with the terminal residues functionalized as esters, and the other being the more hydrophillic uncapped polymer with the terminal residues existing as carboxylic acids.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and a modifications may be practiced within the scope of the appended claims.

What we claim is:

1. A method of preparing a controlled release microcapsule pharmaceutical composition of burst-free sustained, programmable release of a hydrophobic bioactive agent over a duration of 24 hours to 100 days, comprising the steps of:

a) mixing a hydrophobic bioagent with a blend of end-capped and uncapped biocompatible, biodegradable poly(lactide/glycolide) copolymer, wherein said end-capped polymer has terminal residues functionalized as esters and said uncapped polymer has terminal residues existing as carboxylic acids; and b) performing a solvent evaporation process to form said microcapsules.

2. The method of claim 1, wherein said copolymer has a molecular weight from 10 to 100 kDa.

3. The method of claim 1, wherein said agent is selected from the group consisting of chemotherapeutics, antibiotics, antivirals, antiinflammatories, cytokines, immunotoxins, anti-tumor antibodies, anti-angiogenic agents, anti-edema agents, radiosensitizers, and combinations thereof.

4. The method of claim 1, wherein said agent is selected from the group consisting of paclitaxel, doxorubicin, 5-fluorouracil, camptothecin, cisplatin, metronicdazole, and combinations thereof.

5. The method of claim 1, further comprising manipulating a ratio of said uncapped polymer and said capped polymer to maximize core loading efficiencies of said hydrophobic bioagent.

6. The method of claim 1, further comprising adjusting a percentage of said capped and a percentage of said uncapped copolymers to stabilize a structure of said microcapsules.

7. The method of claim 1, further comprising increasing an amount of said uncapped polymer relative to said capped polymer to decrease a resulting size of said microcapsules while incorporating said hydrophobic bioagent into said microspheres.

8. The method of claim 1, further comprising manipulating a parameter of acceleration of release of hydrophobic bioagent by adjusting an amount of uncapped polymer, wherein by increasing said uncapped polymer, said acceleration of release increases.

9. The method of claim 1, further comprising manipulating a parameter of acceleration of release of hydrophobic bioagent by adjusting an amount of low molecular weight polymer wherein the greater the amount of low molecular weight polymer, the greater the acceleration of release of said hydrophobic bioagent.

10. The method of claim 1, further comprising manipulating a parameter of acceleration of release of hydrophobic bioagent by adjusting external stir rates in the mixing step, wherein by increasing external stir rates, said release rates are increased.

11. The method of claim 10, further comprising manipulating a parameter of acceleration of release of hydrophobic bioagent by sonification of the polymer and hydrophobic bioagent mixture before performing the external phase stirring.

12. The method of claim 1, further comprising adding sucrose to the polymer and hydrophobic bioagent mixture to increase release rates of the hydrophobic bioagent.

13. The method of claim 1, further comprising cooling the hydrophobic bioagent and said polymer for a first 15 minutes of said mixing to a temperature of 15° C. to form smaller microspheres.

* * * * *